(12) United States Patent
Chodorow et al.

(10) Patent No.: US 9,962,234 B2
(45) Date of Patent: May 8, 2018

(54) DISPOSABLE SURGICAL INTERVENTION GUIDES, METHODS, AND KITS

(71) Applicants: Ingram Chodorow, Rancho Santa Fe, CA (US); Ryan Held, Carlsbad, CA (US)

(72) Inventors: Ingram Chodorow, Rancho Santa Fe, CA (US); Ryan Held, Carlsbad, CA (US)

(73) Assignee: ISETHCO LLC, San Diego, CA (US)

( * ) Notice: Subject to any disclaimer, the term of this patent is extended or adjusted under 35 U.S.C. 154(b) by 170 days.

(21) Appl. No.: 14/720,673

(22) Filed: May 22, 2015

(65) Prior Publication Data

US 2016/0184050 A1    Jun. 30, 2016

Related U.S. Application Data

(60) Provisional application No. 62/096,823, filed on Dec. 24, 2014.

(51) Int. Cl.

| A61C 1/00 | (2006.01) |
|---|---|
| A61C 3/00 | (2006.01) |
| A61C 1/08 | (2006.01) |
| A61B 5/00 | (2006.01) |
| A61B 5/05 | (2006.01) |
| A61B 6/12 | (2006.01) |
| A61B 6/14 | (2006.01) |
| A61B 19/00 | (2006.01) |

(Continued)

(52) U.S. Cl.
CPC ............ *A61C 1/084* (2013.01); *A61B 5/0013* (2013.01); *A61B 5/05* (2013.01); *A61B 5/682* (2013.01); *A61B 6/0492* (2013.01); *A61B 6/12* (2013.01); *A61B 6/145* (2013.01); *A61B 19/54* (2013.01); *A61C 8/0089* (2013.01); *A61C 9/0006* (2013.01); *A61C 19/02* (2013.01); *A61C 19/04* (2013.01); *A61B 6/14* (2013.01); *A61B 6/4452* (2013.01); *A61B 2019/5466* (2013.01); *A61B 2019/5483* (2013.01); *A61B 2560/0214* (2013.01)

(58) Field of Classification Search
CPC ....... A61C 1/082–1/085; A61C 9/0006; A61C 8/0089; A61C 19/02; A61C 19/04–19/055; A61C 5/08–5/88; A61B 6/0492; A61B 5/682; A61B 6/145; A61B 6/12; A61B 5/0013; A61B 5/05; A61B 19/54; A61B 6/4452; A61B 6/14; A61B 2019/5466; A61B 2019/5483
USPC ............................ 433/27–29, 49–67, 72–76
See application file for complete search history.

(56) References Cited

U.S. PATENT DOCUMENTS

| 3,878,610 | A | * | 4/1975 | Coscina | ............... | A61C 9/0006 433/37 |
|---|---|---|---|---|---|---|
| 5,302,122 | A | * | 4/1994 | Milne | .................... | A61C 1/084 433/173 |

(Continued)

FOREIGN PATENT DOCUMENTS

| DE | 102005016530 A1 | 10/2006 |
|---|---|---|
| KR | 101199957 B1 | 11/2012 |

*Primary Examiner* — Stephen R Crow
*Assistant Examiner* — Garrett Atkinson
(74) *Attorney, Agent, or Firm* — Troutman Sanders LLP

(57) ABSTRACT

The present invention relates to devices, kits, and methods for planning and carrying out surgical interventions and/or radiographic imaging, particularly dental implant radiographic imaging or surgical interventions.

6 Claims, 20 Drawing Sheets

(51) Int. Cl.
*A61C 8/00* (2006.01)
*A61C 19/02* (2006.01)
*A61C 9/00* (2006.01)
*A61C 19/04* (2006.01)
*A61B 6/04* (2006.01)
*A61B 6/00* (2006.01)

(56) References Cited

U.S. PATENT DOCUMENTS

| | | | |
|---|---|---|---|
| 5,487,664 A | 1/1996 | Weissman | |
| 5,718,579 A | 2/1998 | Kennedy | |
| 5,772,432 A * | 6/1998 | Jordan | A61C 9/0006 433/37 |
| 5,897,509 A * | 4/1999 | Toda | A61C 19/043 33/514 |
| 6,096,048 A * | 8/2000 | Howard, III | A61B 90/10 600/414 |
| 6,223,067 B1 * | 4/2001 | Vilsmeier | A61B 90/16 378/170 |
| 6,296,483 B1 | 10/2001 | Champleboux | |
| 6,319,000 B1 | 11/2001 | Branemark | |
| 6,665,948 B1 | 12/2003 | Kozin et al. | |
| 6,814,575 B2 | 11/2004 | Poirier | |
| 6,971,877 B2 | 12/2005 | Harter | |
| 7,014,461 B2 | 3/2006 | Weinstein | |
| 7,097,451 B2 * | 8/2006 | Tang | A61B 17/176 433/76 |
| 7,322,821 B1 | 1/2008 | Lin | |
| 7,331,786 B2 * | 2/2008 | Poirier | A61C 1/084 433/75 |
| 7,346,417 B2 | 3/2008 | Luth | |
| 7,457,443 B2 * | 11/2008 | Persky | A61B 6/14 128/922 |
| 7,650,924 B1 | 1/2010 | Bouldin | |
| 7,762,814 B2 * | 7/2010 | van der Zel | A61C 1/084 433/201.1 |
| 7,831,786 B2 | 11/2010 | Viswanathan | |
| 7,905,726 B2 * | 3/2011 | Stumpel | A61C 1/084 433/196 |
| 8,105,081 B2 | 1/2012 | Bavar | |
| 8,129,703 B2 * | 3/2012 | Sirat | A61B 5/0088 250/208.1 |
| 8,172,573 B2 * | 5/2012 | Sonenfeld | A61C 1/084 433/173 |
| 8,215,957 B2 * | 7/2012 | Shelton | A61C 1/084 433/75 |
| 8,231,386 B2 | 7/2012 | Hertz | |
| 8,348,669 B1 | 1/2013 | Schmitt | |
| 8,398,396 B2 | 3/2013 | Taormina et al. | |
| 8,535,055 B2 | 9/2013 | Katz | |
| 8,585,402 B2 * | 11/2013 | Vogel | A61C 1/084 433/72 |
| 8,690,569 B2 * | 4/2014 | Machado et al. | A61C 1/084 433/72 |
| 8,714,975 B2 * | 5/2014 | Stumpel | A61C 1/084 433/75 |
| 8,750,590 B2 * | 6/2014 | Greenberg | A61B 6/14 382/131 |
| 8,764,440 B2 * | 7/2014 | Haber | A61C 1/084 433/72 |
| 8,794,964 B2 | 8/2014 | Haber | |
| 8,821,159 B2 | 9/2014 | Lo et al. | |
| 8,827,699 B2 | 9/2014 | Bavar | |
| 8,892,235 B2 | 11/2014 | Choi et al. | |
| 8,905,758 B2 | 12/2014 | Yang | |
| 8,938,282 B2 * | 1/2015 | Daon | A61B 5/064 600/407 |
| 9,283,055 B2 * | 3/2016 | Thompson, Jr. | A61C 1/084 |
| 2004/0157188 A1 | 8/2004 | Luth et al. | |
| 2005/0065433 A1 | 3/2005 | Anderson | |
| 2005/0163342 A1 * | 7/2005 | Persky | A61B 6/14 382/103 |
| 2006/0240378 A1 * | 10/2006 | Weinstein | A61B 5/103 433/76 |
| 2006/0281046 A1 | 12/2006 | Heo | |
| 2008/0085489 A1 | 4/2008 | Schmitt | |
| 2008/0199827 A1 * | 8/2008 | Kamer | A61C 13/0004 433/75 |
| 2010/0137881 A1 | 6/2010 | Kamer | |
| 2010/0143861 A1 * | 6/2010 | Gharib | A61C 19/04 433/81 |
| 2010/0233647 A1 | 9/2010 | Yang | |
| 2011/0208195 A1 | 8/2011 | Palti et al. | |
| 2011/0275032 A1 * | 11/2011 | Tardieu | A61C 8/0089 433/174 |
| 2012/0021372 A1 | 1/2012 | Chen et al. | |
| 2012/0046536 A1 | 2/2012 | Cheung et al. | |
| 2012/0064477 A1 | 3/2012 | Schmitt | |
| 2012/0107764 A1 | 5/2012 | Rizzo | |
| 2012/0148977 A1 | 6/2012 | Shahak et al. | |
| 2012/0316486 A1 | 12/2012 | Cheung et al. | |
| 2013/0017507 A1 * | 1/2013 | Moffson | A61C 1/084 433/27 |
| 2013/0122463 A1 | 5/2013 | Csillag | |
| 2013/0144422 A1 | 6/2013 | Choi et al. | |
| 2013/0309628 A1 | 11/2013 | Orth et al. | |
| 2014/0026419 A1 * | 1/2014 | Haber | A61C 1/084 29/896.1 |
| 2014/0057224 A1 | 2/2014 | Huang et al. | |
| 2014/0057227 A1 * | 2/2014 | Cheng | A61C 1/084 433/173 |
| 2014/0093838 A1 * | 4/2014 | Carmichael | A61C 8/0089 433/76 |
| 2014/0147806 A1 | 5/2014 | Gao | |
| 2014/0178832 A1 | 6/2014 | Choi et al. | |
| 2014/0193769 A1 | 7/2014 | Mackey | |
| 2014/0199650 A1 | 7/2014 | Moffson et al. | |
| 2014/0272773 A1 * | 9/2014 | Merritt | A61B 5/0088 433/29 |
| 2014/0276879 A1 | 9/2014 | Lin | |
| 2014/0287379 A1 * | 9/2014 | Chun | A61C 9/0006 433/42 |
| 2015/0196372 A1 * | 7/2015 | Champleboux | A61B 6/14 433/29 |

* cited by examiner

DISPOSABLE SURGICAL INTERVENTION GUIDES, METHODS, AND KITS

CROSS-REFERENCE TO RELATED APPLICATIONS

This application is claims priority to U.S. Provisional Application No. 62/096,823, filed Dec. 24, 2014. This provisional application is incorporated herein by reference.

TECHNICAL FIELD

The present invention relates to devices, kits, and methods for planning and carrying out surgical interventions and/or radiographic imaging, particularly dental implant radiographic imaging or surgical interventions.

BACKGROUND OF THE INVENTION

In dental surgery, a missing tooth is often replaced by a prosthetic tooth, being anchored to the maxillary or mandibular bone of a patient by means of a dental implant previously inserted into said bone. The installation of dental implants requires an osteotomy to be carried out, which involves the drilling of a bore hole into the maxillary or mandibular bone to create a seat for the successive implant insertion. The bore placement and orientation must be determined carefully before the osteotomy can be carried out. It is important for a successful surgery to ensure that the bore is sufficient to hold and maintain a prosthetic device and that the operation does not damage unintended or adjacent portions of the anatomy of the subject, such as the root of an adjacent tooth or nerves of the lower jaw or maxillary sinus of the upper or lower jaw. Generally, it is recommended that the implant is installed at a stable and precise location and angle and to a precise depth. Further, it is important that the angle created for the prosthetic is correct from a physiological point of view and is in harmony with the other portions of the anatomy of the subject.

Current methods for preparing for an implantation intervention require multiple independent sessions with the dentist and radiologist, often in different locations, prior to carrying out the procedure as well as a fair amount of work on the side of the dentist to prepare a guide model or stent. In addition, current methods require the use of the naked eye of the dentist to ensure proper angulation and depth of the implant bore based on the guide model and information from radiographic scans, thus requiring a highly skilled and trained dentist or surgeon.

SUMMARY OF THE INVENTION

In frequent embodiments, a modular surgical or drill guide assembly is provided, comprising a deformable casting medium defining an open treatment area; and a foundation plate or radiographic guide circumscribing the open treatment area, wherein the foundation plate and the deformable medium are comprised of different materials, and the foundation plate is positioned in contact with the deformable medium. Often, the modular drill guide assembly further comprises a sensor array comprising two or more sensors affixed to the foundation plate. Also often, a guide base is affixed to the foundation plate, wherein the guide base comprises a base opening. The sensors often comprise electromagnetic sensors. In certain embodiments, the foundation plate comprises an open arched material defined by an upper portion and a lower portion, wherein the lower portion is configured to be situated at or below a gumline in the mouth of a subject when positioned on the subject, and the upper portion is configured to be situated at or above the top of the teeth of the subject. The deformable casting medium frequently comprises a putty, a paste, or an epoxy. Often, the deformable casting medium comprises an impression material.

The foundation plate often further comprises laterally extending feet, wherein the laterally extending feet are embedded within the deformable casting medium. Also, the foundation plate often further comprises two or more fiducial markers. Frequently, the foundation plate comprises four fiducial markers.

The modular drill guide assembly often further comprises a sensor array comprising two or more sensors affixed to the foundation plate, wherein the sensors are positioned at or about at the gumline of the subject. Often the sensor array comprises 4 or 8 sensors. The term "affixed" here refers to permanently or releasably attached. Often the sensors are positioned between the upper and lower portions of the foundation plate. Also often, the sensors are positioned below the top of the teeth of a subject. The sensor array comprises a certain embodiment of a manner of sensor placement. In certain embodiments, the sensors comprise paired sensors. Often, the sensor array (whether it comprises paired sensors or otherwise) comprises 3, 4, 6, 8, 9, 12, 15, or 16 sensors. The sensor array frequently further comprises a wireless transponder. The sensor array itself often comprises a separate component attached to the foundation plate. In certain embodiments the sensor array is comprised in the foundation plate, optionally as a single component.

In frequent embodiments, the modular drill guide assembly further comprises a guide collar affixed to the guide base, wherein the guide collar comprises a central opening coaxially situated with the base opening. The central opening is often configured to mate with a drill bit sleeve. The guide base often comprises a separate component attached to the foundation plate.

In certain embodiments, a foundation plate for conducting a surgical operation is provided, comprising an open arched material defined by a first and second upper portion perpendicularly situated to a first and second lower portion, and two or more fiducial markers, each upper portion having a pair of bilateral sloping arms connecting the first and second upper portions to the first and second lower portions, wherein each of the lower portions comprises a laterally extending foot prong. Often, at least one of the pair of bilateral sloping arms comprises an attachment point for a secondary device. Also often, each of the two of more fiducial markers is comprised in the first and/or second lower portion. In certain embodiments, at least one of the lower portions comprises an attachment point for a guide collar or a placement apparatus. The placement apparatus often comprises forceps or fingers. At least one of the lower portions often comprises an attachment point for a secondary device. And, the secondary device often comprises a guide base or a sensor array. The laterally extending foot prong is frequently operable to be inserted into a deformable casting medium and support the foundation plate in contact with the deformable casting medium. In certain embodiments, the open arched material defines an open surgical area that is unimpeded both (a) vertically; and (b) laterally, parallel to the first and second upper portions and above the lower portions. The fiducial markers are most frequently visible in a CT scan. In certain frequent embodiments, the foundation plate comprises a directional mark that indicates the intended orientation of the foundation relative to the mouth of a subject. Often, the directional mark is provided on one or both of the first and second upper portions. In certain embodiments, at least one of the pair of bilateral sloping arms comprises a sensor array attachment point. Often, each of the bilateral sloping arms of the first and second upper portions comprises a sensor array attachment point, wherein at least one of the sensor array attachment points is configured in a different size, shape or orientation than at least one other sensor array attachment point.

In certain frequent embodiments, a sensor array is provided comprising: an open arched material defined by a first and second upper portion perpendicularly situated to a lower portion, each upper portion having a pair of bilateral sloping arms, wherein the lower portion is connected to a bilateral sloping arm of each of upper portions; a sensor comprised in the lower portion; a transponder in communication with the sensor and configured to transmit data received by the sensor to a remote processor. Often, the sensor array further comprises a bisected second lower portion, wherein each portion of the bisected second lower portion is connected to one of the pair of bilateral sloping arms of each of the first and second upper portions. The sensor array also often further comprising a peg situated on the lower portion or on one or more of the sloping arms, wherein the peg is adapted to mate with an attachment point of a foundation plate. The transponder itself often comprises a Bluetooth transponder and/or is powered with a low power battery. The low power battery often provides a short duration of power to the transponder. In certain embodiments, the transponder is removably attachable or attached to the sensor array, or is attachable or attached to the sensor array.

The sensor frequently comprises 3 or more sensors, 4 sensors, between 4 to 8 sensors, 8 sensors, or more than 8 sensors. In certain embodiments, each of the 3 or more sensors is spatially situated in a pre-determined geometric orientation on the sensor array. In certain embodiments, each of the 4 sensors is spatially situated in a pre-determined geometric orientation on the sensor array. In certain frequent embodiments, multiple sensors are paired in a vertical or horizontal plane. In certain embodiments at least one sensor is placed vertically above at least one other sensor. In certain embodiments, two or more sensor pairs are provided, wherein each sensor of the pair is positioned in the same directional plane. This geometric orientation frequently comprises a triangle, square, or rectangle, or another pre-determined shape or orientation. Often, the sensors are arranged so that they surround an open treatment area or implant site when the sensor array is positioned on a subject. The exemplary open arched material of the sensor often defines an open surgical area that is unimpeded both (a) vertically; and (b) laterally from one side, parallel to the first and second upper portions. The sensor of the sensor array frequently comprises an electromagnetic, piezoelectric, or optic sensor.

In certain embodiments, the sensor comprises two or more paired sensors. Often, the sensor array (whether it comprises paired sensors or otherwise) comprises 3, 4, 6, 8, 9, 12, 15, or 16 sensors.

Though not wishing to be bound by any particular theory, presence and use of multiple sensors arranged in a vertical plane relative to one-another provides enhanced accuracy or visual granularity regarding one or more of drill bit or other surgical device depth, vertical speed, tilt angle, or offset angle. Often this vertical plane arrangement of sensors is referred to herein as "paired" or "pairing," though it may involve two or more (e.g., 3, 4, 5, 6, etc.) vertically arranged sensors. In embodiments utilizing a paired arrangement, often multiple additional horizontally-arranged sensors are provided as described herein that may also have a paired arrangement.

In certain embodiments, an angle setting apparatus is provided, comprising: an angle arm moveable along an arced path and configured to hold a collar pin; a swivel plate comprising lingual and buccal indicia; and a guide base holder configured to contain a guide base. The arced path of the apparatus often defines an offset angle, and the swivel plate is often rotatable to define a tilt angle. The angle setting apparatus often further comprises a digital readout, providing an indication of an offset angle and a tilt angle defined by the arced path and swivel plate. The angle setting apparatus frequently further comprises a guide collar, a collar pin, and a guide base, wherein the guide base is contained in the guide base holder, and the collar pin is held in the angle arm in communication with the guide collar positioned on the guide base. Moreover, the angle setting apparatus often further comprises a locking knob in communication with the angle arm and/or the swivel plate to lock the angle arm and/or the swivel plate into a predetermined orientation.

In certain embodiments, a disposable surgical or drill guide kit is provided, comprising: (a) a deformable casting medium; (b) a foundation plate; and (c) a secondary apparatus comprising at least one of one or both of: (i) a sensor array; or (ii) a guide platform comprising a guide base affixed with a guide collar. In other embodiments, a disposable surgical or drill guide kit is provided, comprising: (a) a foundation plate configured to embed within a deformable casting medium; and (b) a secondary apparatus comprising at least one or both of: (i) a sensor array; or (ii) a guide platform comprising a guide base affixed with a guide collar.

In other frequent embodiments, methods are provided for preparing for a dental implant intervention, comprising: forming a registration device, comprising the steps of: (a) applying a deformable casting medium to an anatomical region of a subject; (b) introducing a foundation plate to the deformable casting medium, wherein at least a portion of the foundation plate is embedded into the deformable casting medium; (c) adjusting the foundation plate within the deformable casting medium relative to an implant site; and (d) permitting the deformable casting medium to harden; obtaining radiological scan information of the registration device positioned on the subject within a computer system; and creating a surgical intervention plan comprising a tilt angle, an offset angle, and a depth limitation using the radiological scan information.

In other frequent embodiments, methods are provided for conducting a dental implant intervention, comprising: applying a registration device to an implant site of a subject; affixing a secondary device to the registration device, wherein the secondary device comprises at least one or both of: (a) a sensor array; or (b) a guide platform comprising a guide base affixed with a guide collar introducing a drill bit through the registration device into contact with the implant site; guiding or confirming an orientation and a travel distance of the drill bit in the implant site using (i) the guide platform, and/or (ii) information about the orientation and travel distance of the drill bit obtained from the sensor array. Often, a surgical intervention plan is confirmed prior to introducing the drill bit through the registration device. Also often, the information about the orientation and travel distance of the drill bit comprises real-time information and is displayed on a computer user interface or display. In the methods described herein, the real-time information is frequently displayed together with radiological information of the implant site and registration device.

In certain embodiments, a surgical or drill guide device is provided comprising one or more electromagnetic sensors, wherein the surgical or drill guide is operable to position the one or more sensors at about the gumline of a subject when the surgical guide is removably positioned at an implant site on the subject. In certain embodiments, the one or more electromagnetic sensors comprise paired sensors. In certain embodiments, a surgical or drill guide device is provided comprising a physical guide, wherein the drill guide is operable to position the physical guide at about the gumline of a subject when the surgical guide is removably positioned at an implant site on the subject. In certain embodiments, a hybrid surgical or drill guide device is provided comprising one or more electromagnetic sensors and a physical guide, wherein the drill guide is operable to position the physical guide and the one or more electromagnetic sensors at about the gumline of a subject when the surgical guide is removably positioned at an implant site on the subject. In certain embodiments, a radiographic guide device is provided comprising one or more fiducials, wherein the radiographic guide is operable to position the fiducials at about the gumline of a subject when the radiographic guide is removably positioned at an implant site on the subject. In frequent embodiments, any of these devices is disposable. In related embodiments, kits are provided comprising any one or more of these devices.

DETAILED DESCRIPTION OF THE INVENTION

Figure 1:
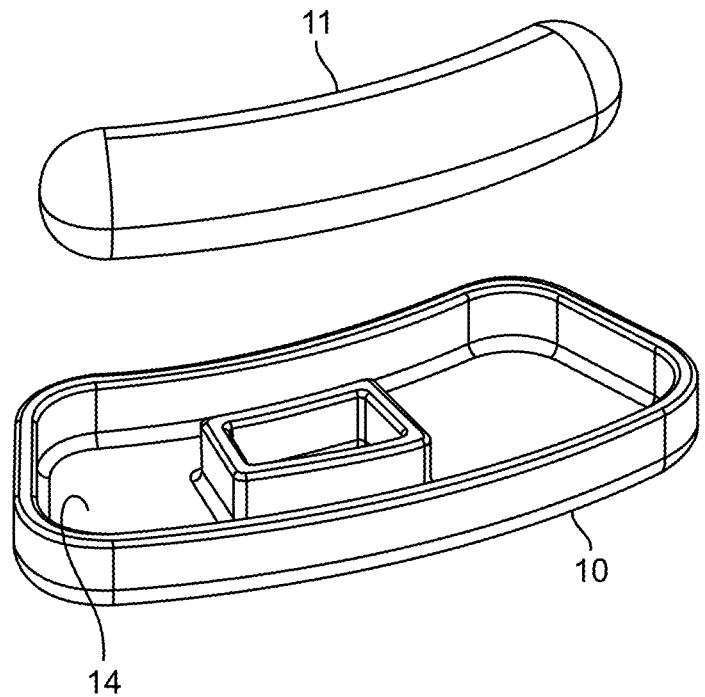
FIG. 1 depicts an exemplary molding tray together with an amount of deformable casting medium.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

The use of the term "embodiment" means that a particular feature, structure, or characteristic described in connection with the embodiment is included in at least one embodiment of described subject matter. As such, the appearance of the phrases "in one embodiment" or "in an embodiment" throughout the present disclosure is not necessarily referring to the same embodiment. Furthermore, the particular features, structures, or characteristics may be combined in any suitable manner in one or more embodiments.

As used herein, "treatment" means any manner in which the symptoms of a condition, disorder or disease are ameliorated or otherwise beneficially altered. Treatment also encompasses any pharmaceutical uses of the devices described herein.

As used herein, "subject" refers to an animal, including, but not limited to, a primate (e.g., human). The terms "subject" and "patient" are used interchangeably herein.

As used herein, "implant site" refers to an area of the anatomy of a subject designated for introduction of a medical implant such as a dental implant, or a site having received a medical implant such as a dental implant.

As used herein, "open treatment area" refers to an area of the anatomy of a patient containing and/or adjacent to an implant site. With reference to a deformable casting medium, an open treatment area refers to an area circumscribed or delineated by the deformable casting medium as an area open and available for a radiological or surgical intervention while the deformable casting medium or registration device is positioned on the anatomy of a subject. An open treatment area is not encumbered or shrouded by the deformable casting medium. An "open treatment area" typically refers to the oral cavity or portion of the jaw of a subject, but may also refer to other portions of the body of a subject requiring surgical intervention and/or radiographic analysis.

As used herein, "dental handpiece" or "handpiece" refers to a tool in medicine, and particularly dentistry, used to drill a hole in the bone, such as a jawbone, of a subject. Drill bits of varying sizes can be used with the handpiece and it is often used in conjunction with various drill bit sleeves to protect and guide the various drill bits. Though drills and drill bits are discussed extensively herein, the present disclosure is equally applicable to additional surgical devices that are capable of being monitored and/or guided using the devices and methods used herein, such as needles, catheters, and surgical cutting tools.

As used herein "anatomy" or "anatomical region" refers to a body portion of a subject. Most frequently, the term anatomy refers to a body portion of a subject designated for receipt of an implant, having received an implant, or an adjacent area. "Anatomy" typically refers to the oral cavity or portion of the jaw of a subject, but may also refer to other portions of the body of a subject requiring surgical intervention and/or radiographic analysis.

As used herein, a "dental implant" or "implant" is a surgical component that interfaces with bone, such as the bone of the jaw or skull, to support a prosthesis (e.g., dental prosthesis) such as a crown, bridge, denture, facial prosthesis or to act as an orthodontic anchor.

As used herein, "about at" or "at about" refer to an approximation. With reference to the location of a sensor or device relative to the anatomy or an anatomical portion of a subject, for example, as exemplified in the Figures. These terms refer most frequently to a vertical distance indication of the spacing of a device or aspect thereof described herein such as a sensor, fiducial, or physical guide relative to the gumline or jawbone of the subject as below the level of the top of the teeth of the subject and above or below the gumline or jawbone of the subject. Teeth need not be present for these terms to maintain their directionally relative meaning. The term "at or about at" refers to "about at" as defined above, as well as positioning of the sensor or device relative to the anatomy or an anatomical portion of a subject "at" a particular location, for example adjacent to, and at the same relative vertical orientation as, the level of a gumline or jawbone. Unless specifically defined otherwise, the terms "top" and "bottom" are directionally relative terms as used herein that are intended to refer to a treatment region of either the upper or lower jaws of a subject comprising teeth, gumline, and jawbone with the teeth at the top and the jawbone on the bottom. When referring to the "top" of the teeth or a tooth, it is intended to encompass the teeth, or a tooth, of both the upper or lower jaw and refers to the part of an intact tooth or set of teeth that is furthest away from the gumline.

As used herein, the terms "upper," "above," "lower," and "below" are used with relative reference to devices, device features, or anatomical structures noted herein. For example, an "upper portion" refers to a portion of a device intended to be at or toward the top of the device or component thereof when in use. Conversely, a "lower portion" refers to a portion of a device intended to be at or toward the bottom of the device or component thereof when in use. The lower portion of a foundation plate, for example, is most frequently positioned at or below the gum line or jawbone of a subject.

As used herein, "deformable casting medium" refers to a putty, paste, epoxy, or the like comprising an impression material that is deformable in a first state and non-deformable in a second or hardened state. The reference to a deformable casting medium herein is, unless specifically stated, intended to be open and without reference to whether the medium is in either a deformable or non-deformable state. In other words, if the medium is hardened, substantially hardened, or in a non-deformable state, it remains to be a deformable casting medium. A variety of materials are contemplated herein as deformable casting mediums, including materials comprised of vinyl poly siloxane, poly ether, polysulfide, alginate, and zinc oxide eugenol paste, among other materials. One example of a commercially available deformable casting medium of the present disclosure comprises impression materials such as Provil® Novo (Heraeus Kulzer, LLC; South Bend, Ind.). Other examples include Exafast (GC America; Alsip, Ill.), Express (3M; St. Paul, Minn.), Genie (Sultan Healthcare; York, Pa.), Impregum (3M; St. Paul, Minn.), Imprint (3M; St. Paul, Minn.), and Position Penta (3M; St. Paul, Minn.).

As used herein, and unless specifically indicated, "dentist" is intended to generally refer to a medical professional in the dental or medical fields, including an assistant to a dentist, doctor, radiologist, or surgeon. As such, those qualified or able to undertake any or all of the procedures set forth herein are intended to be encompassed by the term "dentist."

As used herein, "radiological scan," "radiological imaging," or "radiographic analysis" refers to diagnostic images of anatomic structures through the use of electromagnetic radiation or sound waves. Radiological imaging techniques contemplated herein include, for example, x-rays, computed tomography or computerized axial tomography (CT) scans, positron emission tomography (PET) scans, magnetic resonance imaging and spectroscopy (MRI), and ultrasonograms.

As used herein, "disposable" refers to a device or apparatus intended to be utilized in a single procedure (radiographic, surgical, or both) or with a single subject and then discarded. Often, "disposable" refers to instructions for use or operation of the apparatus or device as intended for disposal after a single procedure or with a single subject. The meaning of "disposable," as used herein, excludes items that are intended to be used with multiple subjects (e.g., items intended to be cleansed/sanitized/autoclaved and re-used on multiple subjects) as well as nonsensical single use applications (e.g., disposing a dental handpiece or CT Scanner after a single use or use with a single subject). Each of the innovative guide devices and apparatuses described herein may be disposable unless specifically indicated.

As used herein, the term "removable" or "removably" refers to a characteristic of a device or apparatus contemplated herein as, or permitting it to be, physically positioned in one location relative to the anatomy of a subject or another device or apparatus and then taken away from that position. This is contrary to permanent placement via screws, staples, stitches, bolts, adhesive or the like. For example, "removable" or "removably" excludes attachment of a device and/or its associated components to the anatomy of a subject via surgical intervention such as through the use of a screw inserted into a tissue of the subject.

As used herein, "fiducial" refers to a fiducial marker or object that when placed in the field of view of an imaging system, such as a radiographic scan, appears in the image produced.

As used herein, "surgical intervention" refers to a physical intervention on one or more tissues of a subject.

Subject evaluation for implantation purposes is a process where a subject is assessed to determine whether they are a candidate for an implant. A variety of factors are taken into account in this process, including the status of the site of the implant, including the positioning and morphology of anatomical landmarks at and near the site. Subject evaluation often mandates a 3-dimensional radiographic scan such as a CT scan, which provides a 3-dimensional view of the subject anatomical structures. In some embodiments, the 3-D radiographic scan provides a 3-dimensional computer representation of the dentition, maxilla and/or mandible and associated dental structures of the subject (i.e., the anatomy of the subject) by virtue of cross-sectional images as known in the art. In some embodiments, the 3-dimensional radiographic scan provides a controllable 3-dimensional image using computer graphic methods well-known in the art. The 3-dimensional radiographic scan is stored in the system for later operation.

The present disclosure is intended to enhance and ease the patient evaluation process, increase the amount of useable information obtained from scans such as CT scans, and to increase accuracy and minimize risks of undertaking surgical interventions such as implant procedures.

According to the present disclosure, and with reference to the devices and systems described herein, a typical subject would be exposed to and/or benefit from at least some of the following processes and procedures. A subject at some point in the process presents to a dentist with a surgical intervention site such as an implant site.

Foundation Plate and Registration Device

Figure 2:
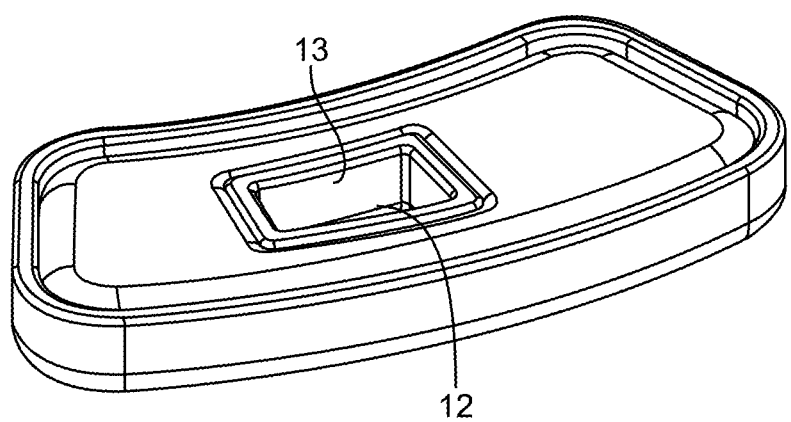
FIG. 2 depicts an exemplary molding tray containing deformable casting medium.
Figure 3:
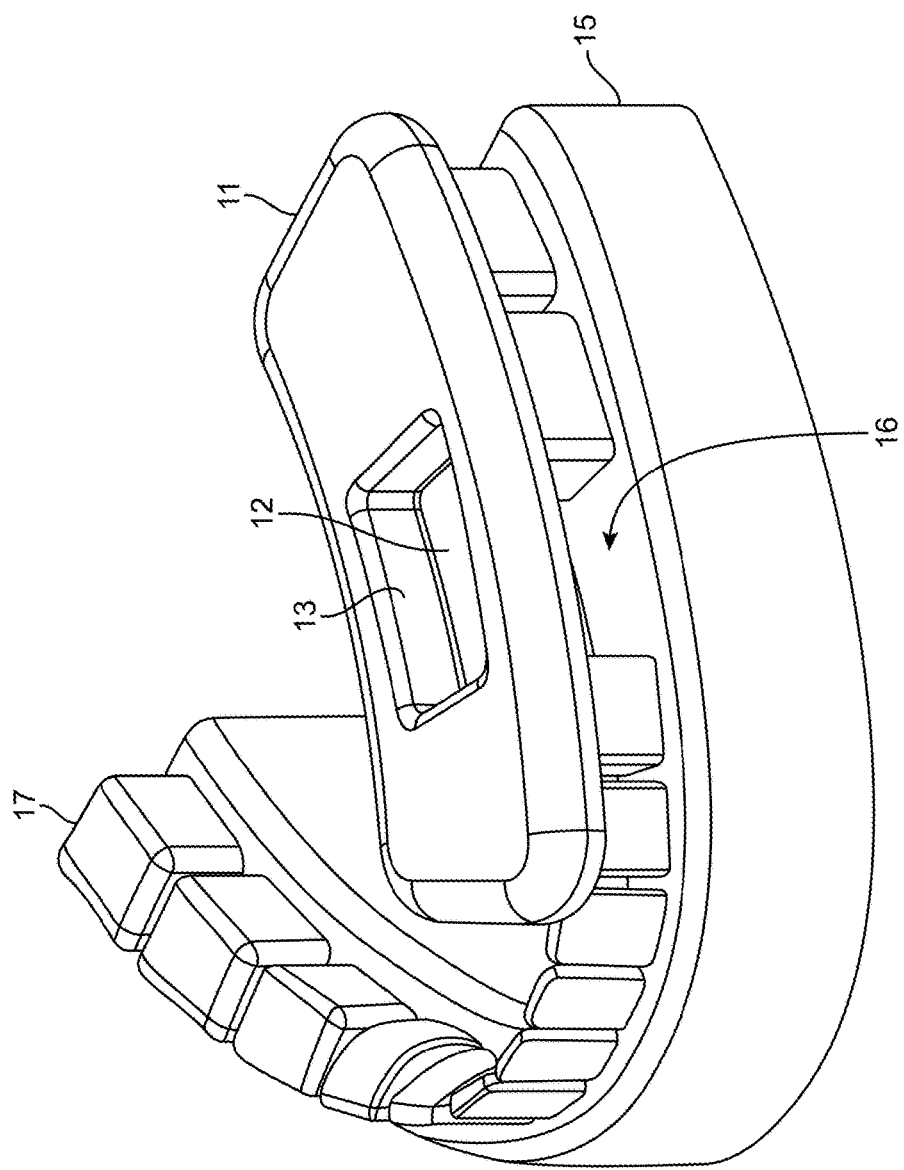
FIG. 3 depicts an exemplary molding tray positioned above an implant site of a model anatomy.
Figure 4:
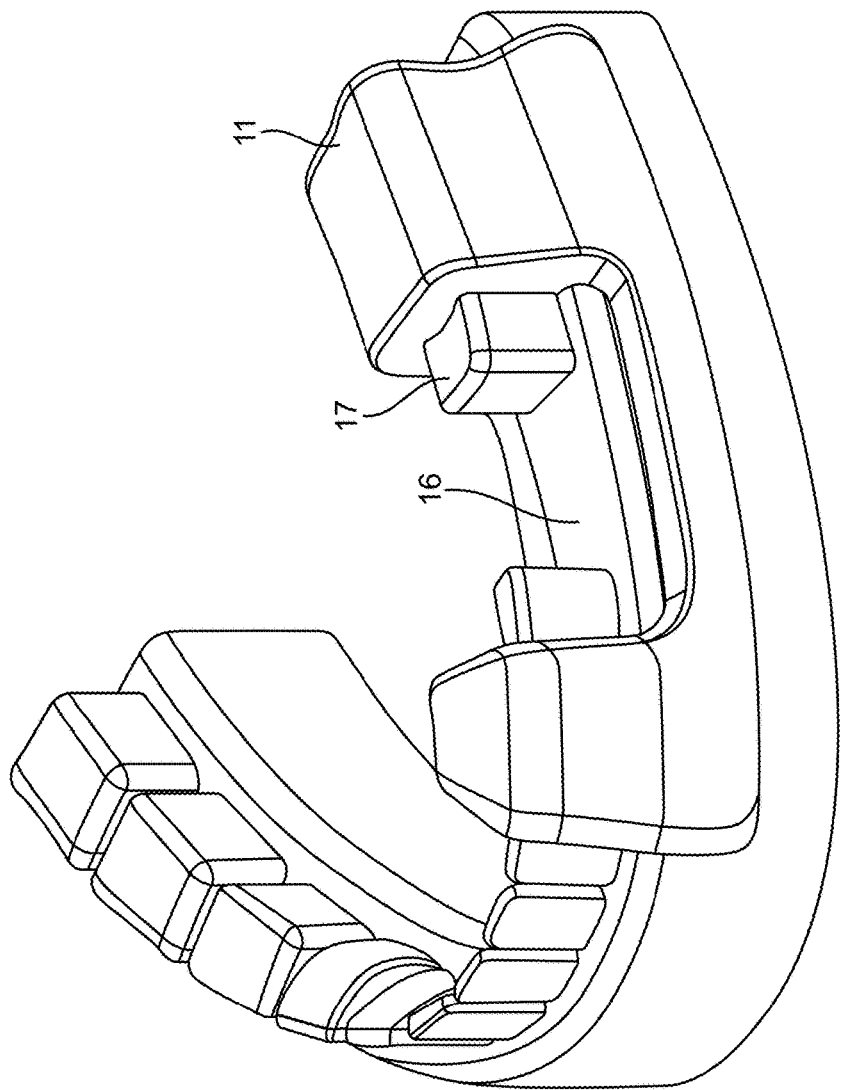
FIG. 4 depicts deformable casting medium formed around the teeth of a model anatomy, surrounding an implant site.
Figure 6:
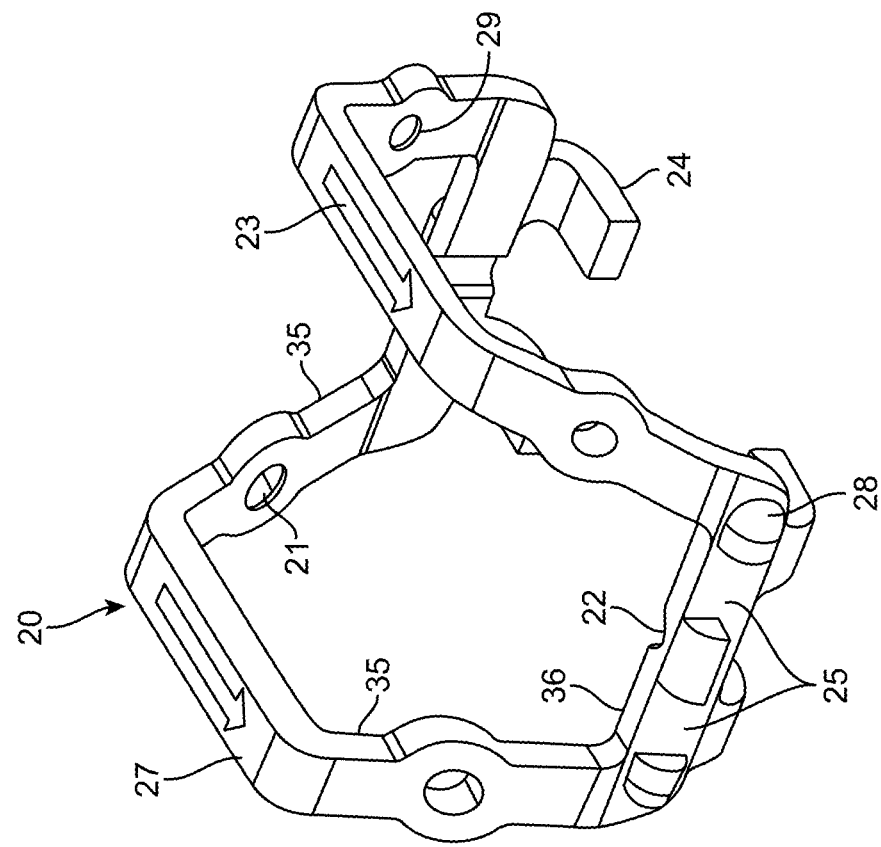
FIG. 6 depicts a perspective view of an exemplary foundation plate of the present disclosure.
Figure 5:
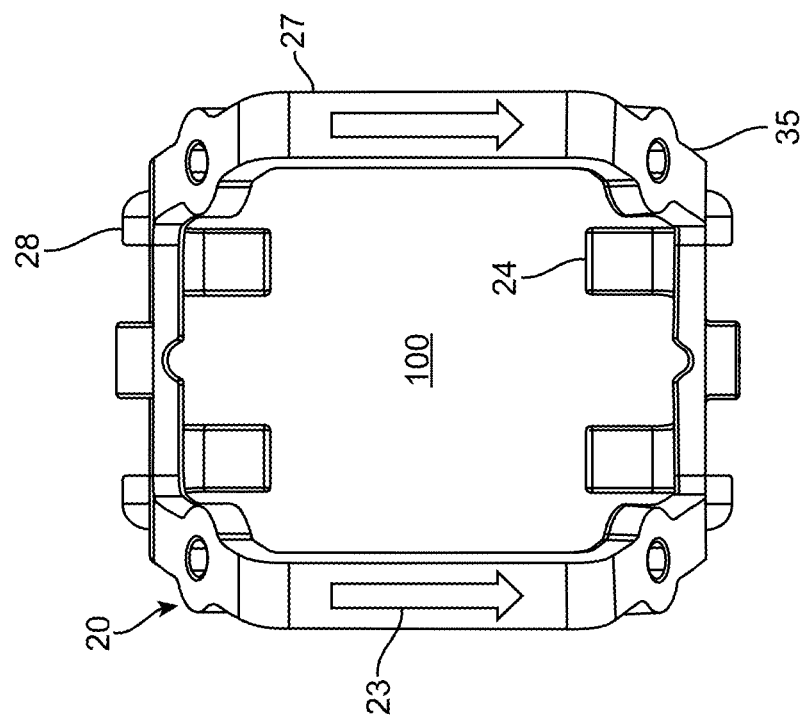
FIG. 5 depicts a top view of an exemplary foundation plate of the present disclosure.

With reference to FIGS. 1 and 2, the dentist or dental assistant measures out and mixes a deformable casting medium such as impression putty 11. The dentist then places the fully mixed putty 11 into the inner portion 14 of a molding tray 10. In an exemplary molding tray 10, a treatment area void 12, optionally defined by walls 13, is included. The treatment area void 12 defines a treatment area devoid of the deformable casting medium 11. In frequent embodiments, the treatment area void 12 is dimensioned to match the implant site 16, between existing teeth in the subject. This dimensioning eases the shaping of the deformable casting medium 11 to match the implant site and surrounding regions of the subject's anatomy 15, 17 to facilitate later steps of the procedure. The resulting effect of this can be seen, for example, in FIG. 4 where the deformable casting medium 11 surrounds the implant site 16. As can be seen in FIGS. 3 and 4, the dentist the removes the deformable casting medium 11 and places it over the implant site 16, forming it to the teeth 17. Though molding tray is often not necessary to the present methods, it eases the accurate placement of the deformable casting medium on the anatomy of the subject.

With reference to FIGS. 5-8, the dentist utilizes a tool such as rubber dam clamp forceps to manipulate the prongs 24 of a foundation plate 20 (also referred to herein as a "radiographic guide") into the deformable casting medium 11 in a desired orientation circumscribing the implant site 16. Often the foundation plate 20 is provided with directional indicia 23 to facilitate proper placement of the foundation plate 20. In the depicted example, directional indicia 23 (e.g., arrows) face the outside of the mouth of the subject.

An exemplary foundation plate 20 has a variety of features, exemplified in the Figures and briefly described as follows. In the depicted example, the foundation plate 20 is an open arched contiguous loop of material, which can be the same or different materials and may comprise an assembly of materials having the same or different physical characteristics. The material of the foundation plate 20 can be any of a variety of types of plastics and/or metals and can be molded, assembled, milled, or 3-D printed. Geometrically, the exemplary foundation plate 20 is defined by upper portions 27, each having bilateral sloping arms 35, having attachment points 21, 29 for a secondary device such as a sensor array 40 (FIGS. 14, 16-17, 26). The bilateral sloping arms 35 may be the same or different material and shape as the upper portions 27, and their delineation is generally indicated by a bend or different angulation versus a respective upper portion 27. In certain limited embodiments the upper portion 27 is comprised as a bend extending between, simply an intersection between, or the top/ends of, two separate bilateral sloping arms 35. The attachment points can be of the same or different size, shape, or orientation. In the exemplary foundation plate 20, attachment points 21 are comprised of holes in the material that are larger than the holes comprising attachment points 29. Providing different size, shape, or orientations for the attachments points has been found to be useful to ensure proper orientation of the sensor array 20. Moreover, if the exemplary sensor array 40 is intended to become a permanent fixture on the foundation plate 20 once it is attached, providing size, shape, or orientations of the attachment points 21, 29 facilitates removal and proper placement of the sensor array 40 if initially installed in an incorrect orientation on the foundation plate 20.

In certain embodiments, the particular geometric arrangement of supportive features of the foundation plate is not important to achieve the overall purpose of providing a base for situating a sensor array and/or physical guide, while not vertically or laterally inhibiting or obstructing a treatment area. In this regard, the foundation plate may be comprised of multiple units assembled together. So, although a preferred embodiment involves bilateral sloping arms, such an arrangement is not required. One objective of the foundation plate is to permit accurate, and optionally removable, placement of sensors or a physical drill guide relative to a surgical site such as an implant site or open treatment area. This placement is most frequently at the level of a tissue of the patient (e.g., gum line or jawbone) where a drill or another surgical device will penetrate the tissue. This level is frequently immediately adjacent of the tissue. Often, in a dental implant embodiment this placement is between the level of the top of the teeth of the subject and the gum line or jawbone. As such, regardless of the physical configuration, a foundation plate of the present disclosure addresses these and other objectives pertinent to placement of guides and sensors as close as possible to the level of tissue where the surgical intervention is to occur, and other objectives.

Lower portions 36 connect each of the arms 35 of the foundation plate 20 and can be the same size, shape, orientation or can differ in one or more of these aspects. Often, when one of the lower portions 36 differs from another lower portion in the same foundation plate it is for the purpose of directional orientation of a separate device such as a sensor array 40, foundation plate adjuster 30, or guide base 80. The lower portions 36 are often defined by one or more of the following features. Most frequently the lower portions 36 include laterally extending feet (also referred to as prongs) 24 for insertion into a deformable casting medium 11. Four prongs 24 are depicted, but fewer or additional prongs could be included, and their size and shape could be altered as long as they serve the function of supporting the foundation plate 20 within the deformable casting medium 11.

Figure 9:
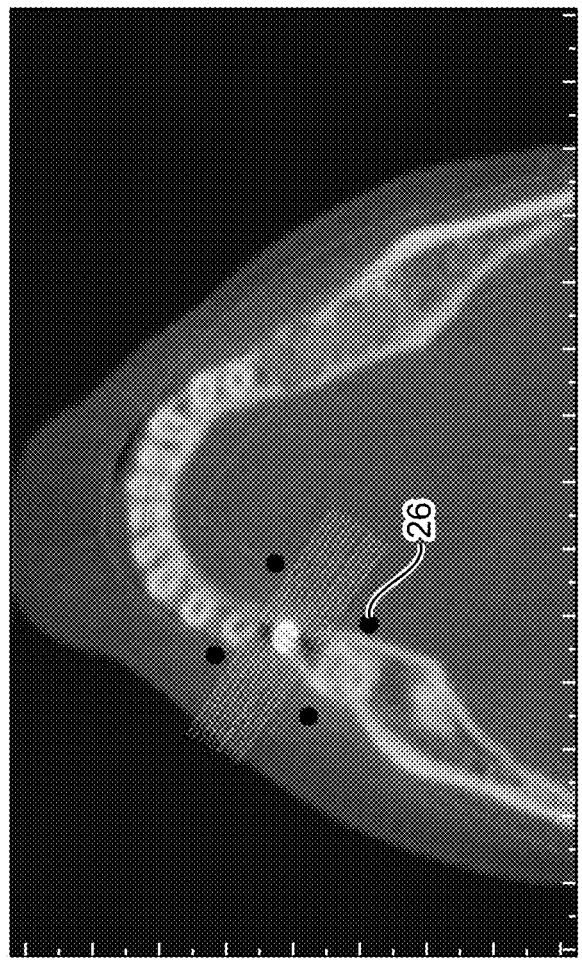
FIG. 9 depicts a CT scan of a subject, showing the location of the fiducial markers of the exemplary foundation plate relative to the anatomy of the subject.
Figure 8:
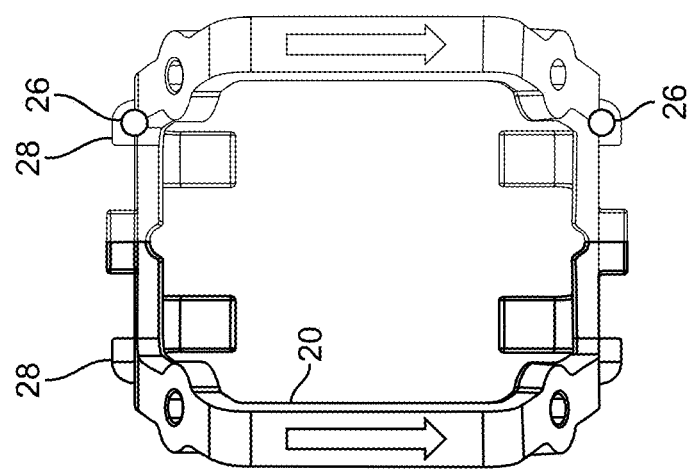
FIG. 8 depicts another top view of an exemplary foundation plate of the present disclosure showing the locations of two fiducial markers.

The lower portions 36 also frequently include fiducial marker areas 28 containing or comprising fiducial markers 26, which in the depicted example provide them in the shape of a square. Other simple geometric orientations of the fiducial markers 28 are contemplated, such as triangle or rectangle, though square orientation is most frequently preferred. The fiducial markers 26 can be embedded, encased, or attached to the lower portions 36 and are limited to materials that show up, or are noticeably absent, when subjected to radiographic imaging such as by way of an X-ray, CT scan, or MRI. See FIG. 9. The fiducial markers generally create size and position context relative to a subject's anatomy, and assures precise correlation between anatomy and a radiographic scan such as a CT scan. Fiducial markers 26 of the present disclosure are generally recognized by implant software contemplated herein. Metal balls are one example of a fiducial marker 26 contemplated herein. Also optionally present on the lower portions 36 are forceps notches 22 to permit simplified gripping and placement into a deformable casting medium 11 using rubber dam clamp forceps. Interface aspects for use in conjunction with similar devices are also contemplated. Moreover, the lower portions 36 also most frequently include features 25 serving as attachment points for a separate device such as a foundation plate adjuster 30 or guide base 80.

The foundation plate 20 is frequently provided in an orientation and is comprised of materials that provide resiliency to permit the lower portions 36 to be spread away from one another and, without additional input, they spring back to their original or approximately original shape or orientation. In certain embodiments, the foundation plate is provided with an actuating mechanism (not depicted) that permits it to be oriented in a first open position and upon activating the actuating mechanism, the lower portions are induced to move to a second closed position. Without regard to whether a mechanism is present or not, an open position refers to a position permitting the foundation plate 20 to be placed around a deformable casting medium 11 or an open treatment area, and a closed position refers to a position where the prongs 24 are gripping, or positioned to grip, a deformable casting medium 11 or the anatomy of a subject.

The foundation plate exemplified herein is not intended to be limited to any particular materials or physical arrangement with the limitation that it provides reliable placement of a fiducial, a sensor, and or a physical guide at about the anatomy or implant site of a subject (such as a gumline) intended for radiographic investigation or surgical intervention.

Figure 7:
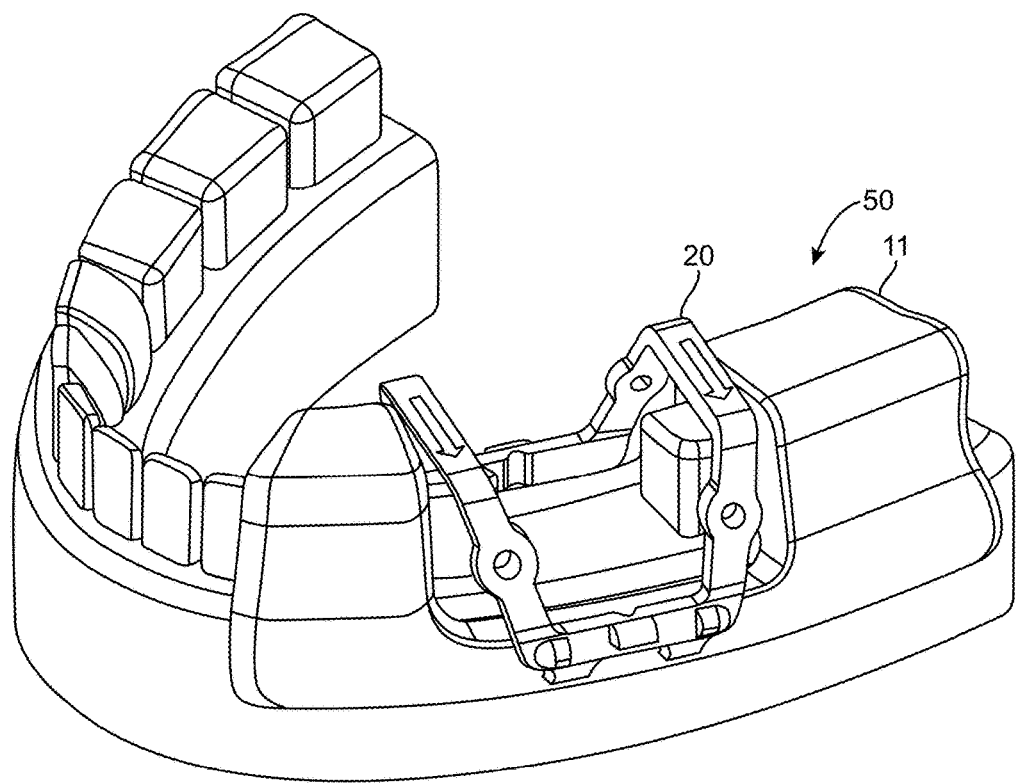
FIG. 7 depicts an exemplary foundation plate embedded into the deformable casting medium formed around the teeth of a model anatomy, together forming an exemplary registration device.

Referring to FIG. 7, when placing an exemplary foundation plate 20, it is gripped by an attachment apparatus such as forceps and the lower portions 36 are spread laterally or tensioned away from one-another. The foundation plate 20 gripped by the attachment apparatus is then lowered over a deformable casting medium 11 previously applied to the oral features 15, 17 of the subject surrounding an implant site 16 or the anatomy of the subject. When positioned at an approximately correct location circumscribing an implant site 16, the tension is released between the bilateral sloping arms 35 and the prongs 24 are permitted to contact and embed within the deformable casting medium 11. This process is generally undertaken in short order after the deformable casting medium 11 is placed in the subject so that the casting medium is still in a malleable state, permitting easy placement and embedding of the prongs into the medium. These deformable mediums are well known in the art and have known timing and parameters for hardening.

In certain embodiments, the foundation plate is positioned around or adjacent to an open treatment area, implant site, or anatomy of a subject without the use of a deformable casting medium.

Figure 10:
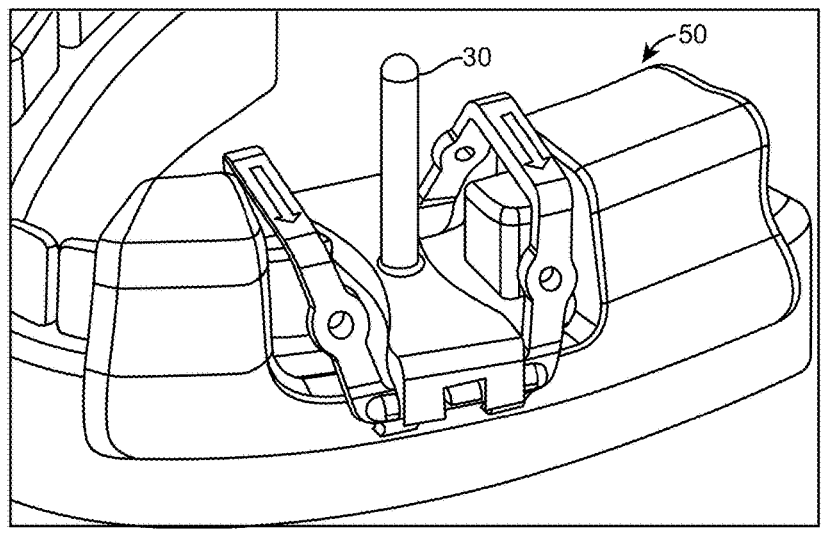
FIG. 10 depicts an exemplary foundation plate adjustor engaged with the foundation plate of an exemplary registration device positioned around the teeth of a model dentiture.
Figure 11A:
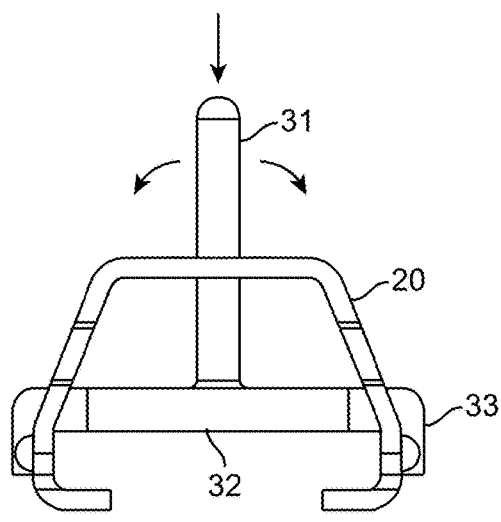
FIG. 11A depicts a side view of an exemplary foundation plate adjustor engaged with an exemplary foundation plate.
Figure 11B:
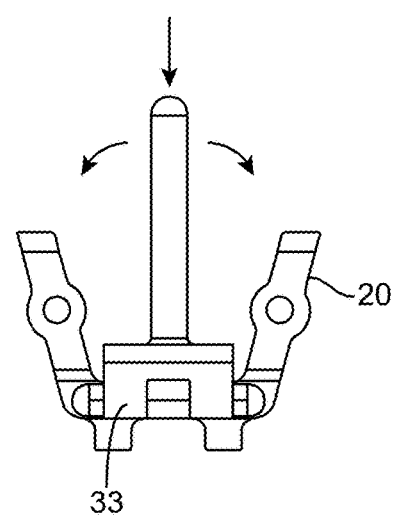
FIG. 11B depicts a front view of an exemplary foundation plate adjustor engaged with an exemplary foundation plate.

With reference to FIGS. 10 and 11A-B, once the foundation plate 20 is positioned circumscribing an implant site and at least partially embedded in the deformable casting medium 11, it may be optionally adjusted using a foundation plate adjuster 30, which is attachable to or surrounding lips 25 of the foundation plate 20 using exemplary features 33. As depicted in FIGS. 11A and 11B, the dentist uses the foundation plate adjuster to check the spread, depth, and/or angulation of the foundation plate. The handle 30 can be used to manipulate base 32 and lips 33 and, as a result, the foundation plate 20 is manipulated. FIG. 11A provides a side view, indicating that manipulation can be side to side or vertically. FIG. 11B provides a front view, also indicating that manipulation can be side to side (i.e., a first and second lateral direction) or vertically. It will be understood by one of skill in the art that movement side-to-side here may frequently involve movement in an arc from side-to-side. Typically, the lower portions 36 are pushed down to the gumline and one or more of spread and angle of the foundation plate 20 on the subject are manipulated and set.

Figure 12A:
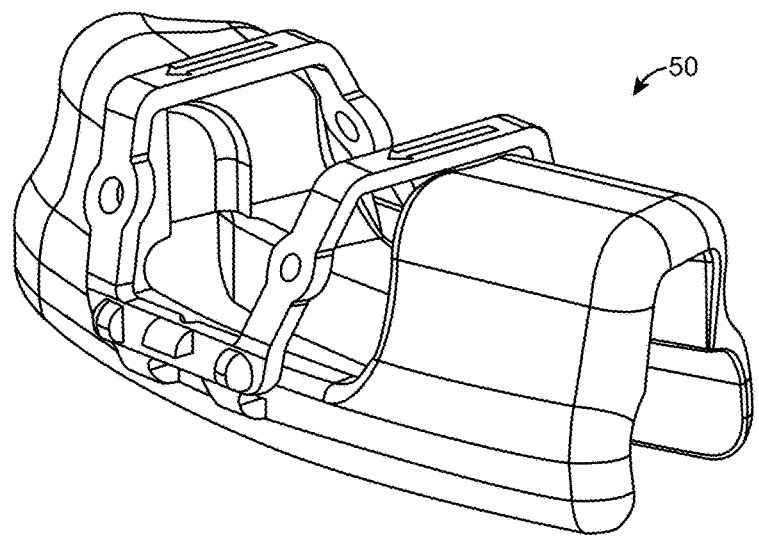
FIGS. 12A, 12B, and 12C depict various views of an exemplary registration device.
Figure 12B:
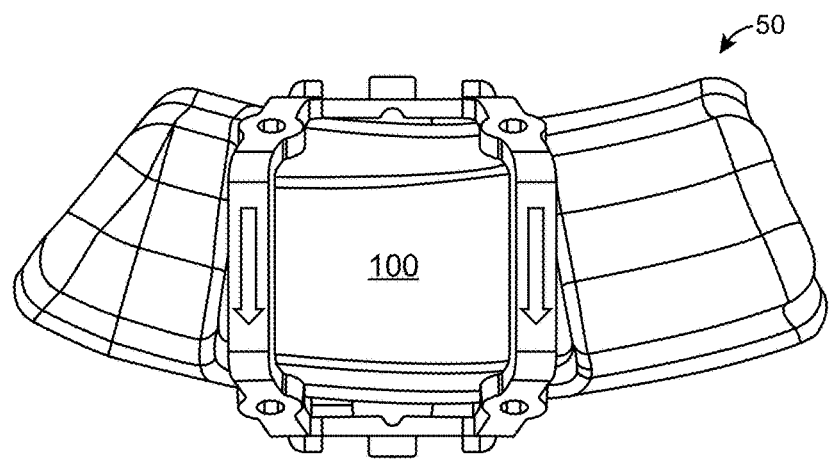
Figure 12C:
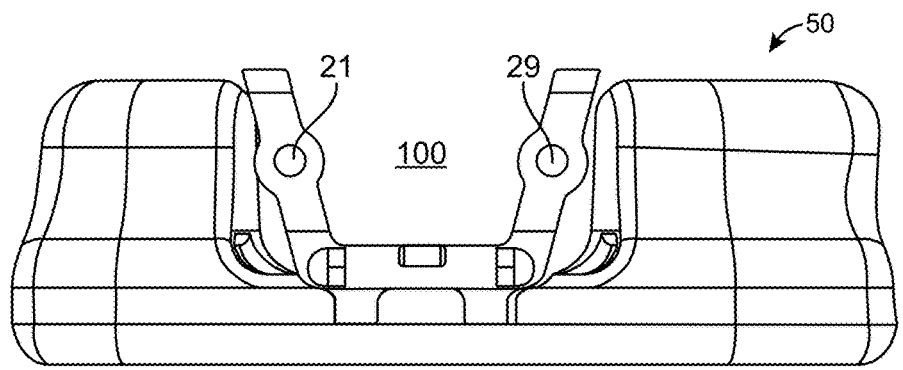

With reference to FIGS. 12A-12C, once the proper spread, depth, and angle has been set, the dentist will let the deformable casting medium 11 cure or harden around the various anatomical features of the subject. Once cured, the foundation plate 20 will be set in the hardened deformable casting medium 11, creating a registration device 50 comprised of the deformable casting medium 11 and the foundation plate 20. The registration device 50 can then be removed from the mouth of the subject and reliably replaced in its original location for radiographic investigation or surgical intervention. In certain embodiments, the registration device 50 is removed and brought with the subject to obtain a radiographic (e.g., CT) scan at a location remote from the location where it was made. For example, the subject may have to go to a different room or location, immediately thereafter or at a later time or day, to obtain a radiographic scan.

Figure 13:
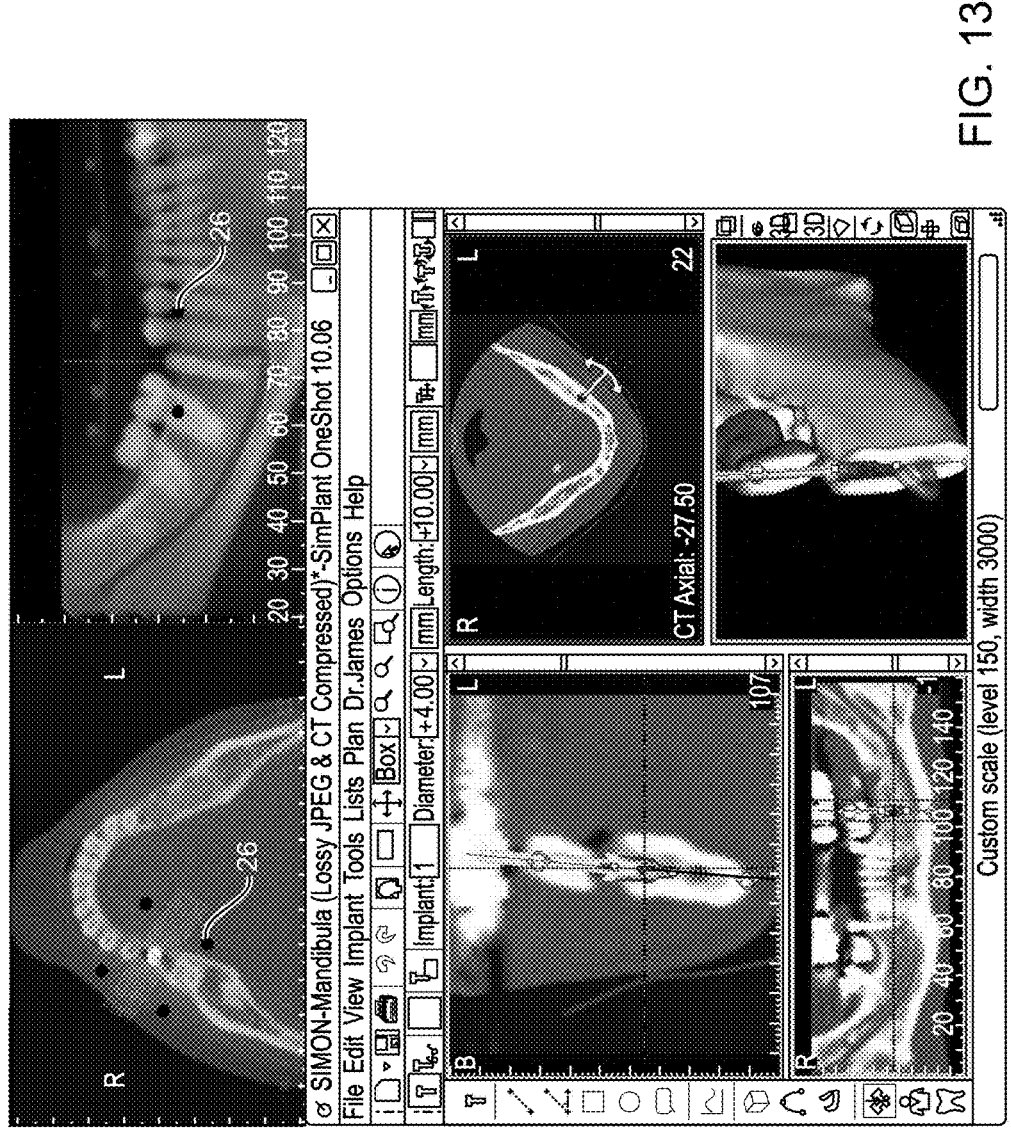
FIG. 13 depicts an exemplary implant plan based on a CT scan of a subject generated using implant software.

At the time of the radiographic scan, the subject, doctor or dentist places the registration device 50 on their anatomy prior to the scan. As depicted in FIG. 13 (and FIG. 9), the fiducials in the foundation plate 50 show up in the CT scan and allow the implant software to record or evaluate the size and position of the registration device. The CT scan establishes, for example, maximum depth, probable maximum implant diameter, precise angle for tilt (front to back) for the implant, and angle offset (side to side) for the implant. With the CT scan results, the dentist then creates an implant plan using any of a variety of commercially available implant software programs. An algorithm is used based on the locations and positions of the fiducials identified in the radiographic scan that defines a plane relative to the anatomy of the subject, and calculates tilt, offset, and depth for the implant. Often, a guide path for the drill bit is defined by the implant software. The determination of the positions of the fiducials may include the steps identifying each fiducial and a relationship of each relative to each other and/or the anatomy of the subject. In certain embodiments, the relative size or intensity of each fiducial in the radiographic scan provides an indication of location and/or to depth of each fiducial.

In certain embodiments, the registration device 50 is used to generate radiographic scans of the implant site and is not used during the implantation procedure. In certain other embodiments, the registration device 50 is used to generate radiographic scans of the implant site and is used during the implantation procedure alone, or together with a sensor array 40, a physical drill guide 96, or a hybrid physical and sensor drill guide 97.

Sensor Array

With reference to FIGS. 14-17, the dentist is provided the registration device 50 and refers to implant software. The dentist then opens a fresh sensor array 40 package and activates it, for example, by depressing the sensor activation button 52 on the transponder 41. The computer system containing the implant software then wirelessly acknowledges the new sensor and inquiries if it has acknowledged the correct sensor for connection. Frequently, each sensor will have a unique identifier, electronic or otherwise, that is transmitted and picked up by the computer system and implant software to ensure that the correct sensor is utilized in the procedures that follow. The dentist is frequently provided an opportunity on the software to accept or reject the particular sensor identified by the software. In frequent embodiments, the dentist verifies the operability of the sensor array 40 by passing, for example, a standard such as a magnetized drill bit 55 or another device or standard through the center area 100 of the sensor array 40, simulating at least an approximation of the intended drilling path. Often, the monitor of the computer system containing the implant software will display a representation of the standard (e.g., virtual drill bit 55) as it passes through center area 100, if working properly. This process often occurs prior to attaching the sensor array 40 to the registration device 50, but may occur after attachment as well.

Upon confirmation of the working sensor array 40, the dentist then attaches the sensor array 40 to the registration device 50. The dentist then places the combined device onto the anatomy of the subject and begins the implant procedure, using visual feedback on the computer monitor. In related embodiments, the registration device may be placed on the anatomy of the subject prior to attachment of the sensor array 40.

In frequent embodiments, directional indicia 46 showing proper placement of the sensor array are provided. In the depicted example, the directional indicia 46 are arrows that point out toward the cheek of a subject when properly oriented and in the mouth of a subject. The dentist attaches the sensor array 40 to the registration device 50 upon aligning the directional indicia 46 of the sensor array 40 with the directional indicia 23 of the foundation plate 20. The sensor array 40 optionally includes pegs 44, 49 of multiple sizes that match with the size of the attachment points 21, 29 of a foundation plate when oriented in the proper direction. In certain frequent embodiments, the registration device 50 and sensor array 40 are devices that are intended to be disposable and useable with a single patient. In these circumstances, the mating of the sensory array 40 with the registration device 50 is intended to be a permanent mating or a mating that requires significant effort to remove the sensory array 40 after attachment. The use of different sized pegs 44, 49 and attachment points 21, 29 is useful in these embodiments as it ensures that the sensor array 40 cannot be mated with the registration device improperly. In a typical embodiment, the sensor array 40 slides over top of the foundation plate 20 and the sensor pegs 44, 49 engage attachment points 21, 29 in the foundation plate 20.

Similar to the foundation plate 20, the sensor array 40 is frequently comprised of an open arch of material, which can be the same or different materials and could comprise an assembly of materials having the same or different physical characteristics. The material of the sensor array 40 can be any of a variety of types of plastics and/or metals and can be molded, assembled, milled, or 3-D printed. Geometrically, the exemplary sensor array 40 is designed to mate with the geometry of the foundation plate 20. Frequently, the sensor array 40 is defined by upper portions, each having bilateral sloping arms, having pegs 44, 49 for attachment to a foundation plate 20 (FIGS. 14C, 16-17, 26). The bilateral sloping arms may be the same or different material and shape as the upper portions, and their delineation in exemplary embodiments is generally indicated by a bend or different angulation versus a respective upper portion. In certain limited embodiments the upper portion is comprised as a bend extending between, simply an intersection between, or the top/ends of, two separate bilateral sloping arms. The pegs can be of the same or different size, shape, or orientation; or another physically integrating aspect or mechanism is useable in replacement or together with the exemplified pegs, with the requirement that the sensor array 40, or portion thereof, mate with the foundation plate 20 or registration device in a pre-determined manner or orientation.

Lower portions 43, 45 connect at least two of the arms of the sensor array 40 and can be the same size, shape, orientation or can differ in one or more of these aspects. Most frequently, lower portions 45 are comprised of two physically separated or unconnected portions. Though lower portions 45 are connected with the arms of the sensor array 40, their separation defines a gap that is vertically and/or laterally unimpeded to center area 100. Importantly, the sensor array most frequently includes a gap that is vertically and/or laterally unimpeded to center area 100. This gap will generally face toward the outside of the mouth of the subject, i.e., the area from which the dentist approaches the implant site 16. This gap provides both physical and visibility access to center area 100, which when the device is placed on the anatomy of the subject, defines at least a portion and preferably all of the implant site 16. Therefore, in the most frequent embodiments, the use of the sensor array does not alter the physical or visibility access to, or methods of accessing, the implant site 16.

Figure 14B:
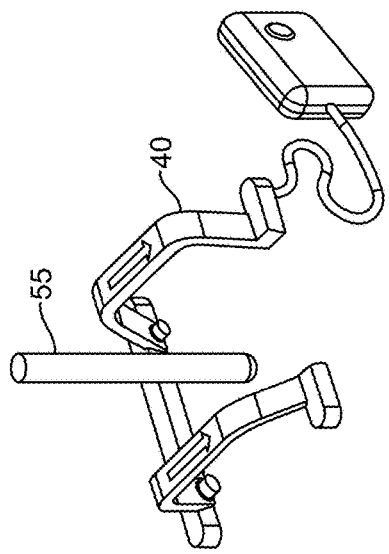
FIG. 14B depicts a perspective view of an exemplary sensor array of the present disclosure together with a magnetized drill bit.
Figure 15:
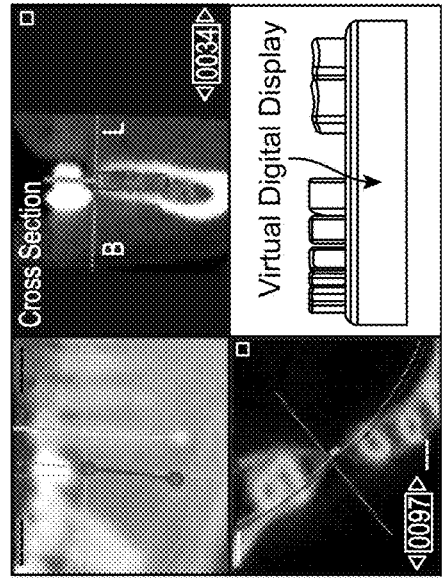
FIG. 15 depicts an exemplary display of a drill bit in operation relative to a registration device positioned on the anatomy of a subject.
Figure 14A:
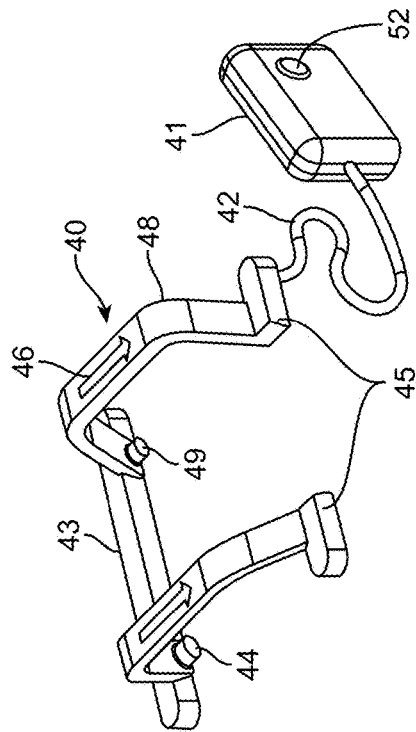
FIG. 14A depicts a perspective view of an exemplary sensor array of the present disclosure.
Figure 14C:
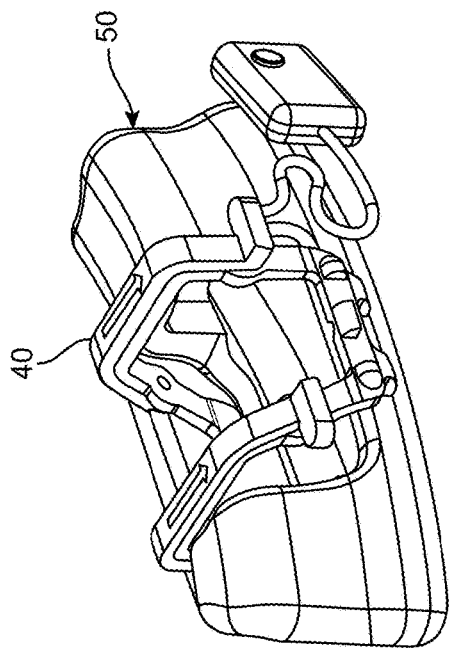
FIG. 14C depicts a perspective view of an exemplary sensor array of the present disclosure mated with the foundation plate of an exemplary registration device.
Figure 16B:
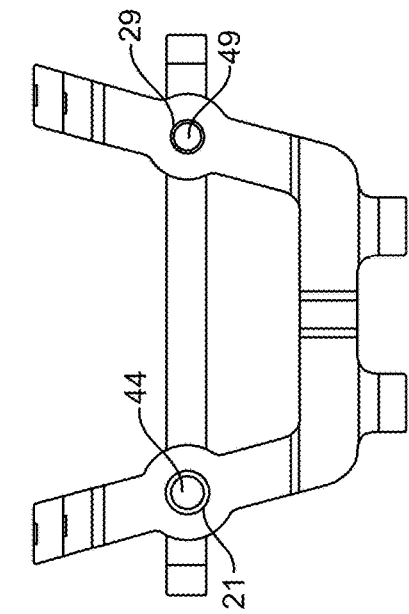
FIGS. 16A, 16B, and 16C depict various views of an exemplary sensor array separate from and engaged with an exemplary foundation plate.
Figure 16C:
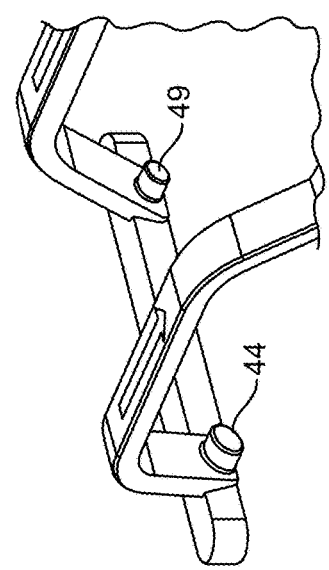
Figure 16A:
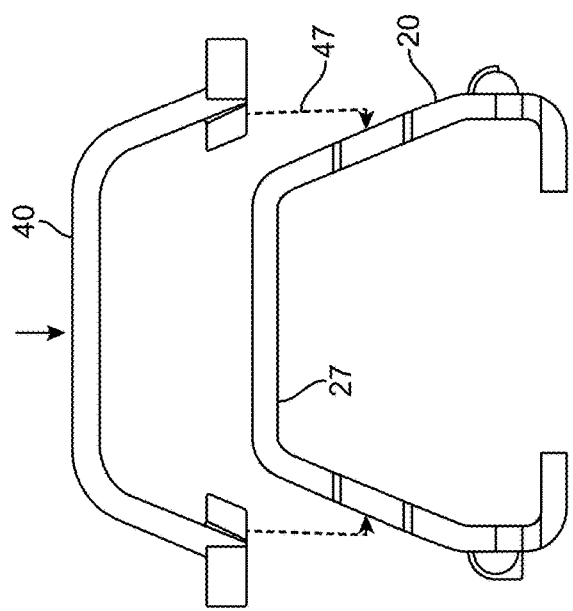
Figure 16D:
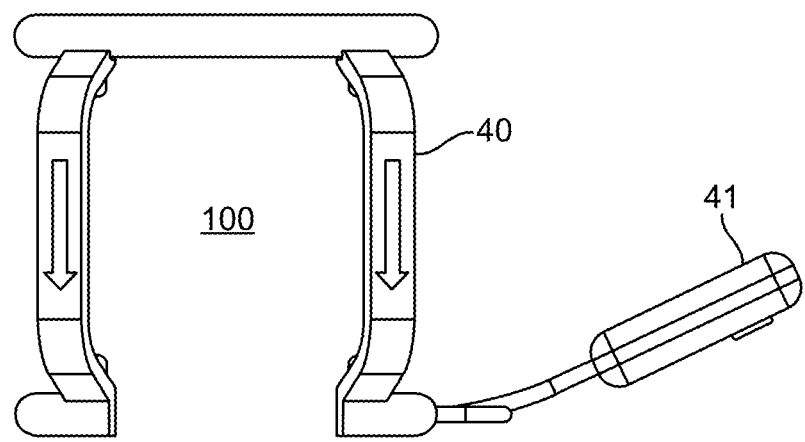
FIG. 16D depicts a top view of an exemplary sensor array.
Figure 27A:
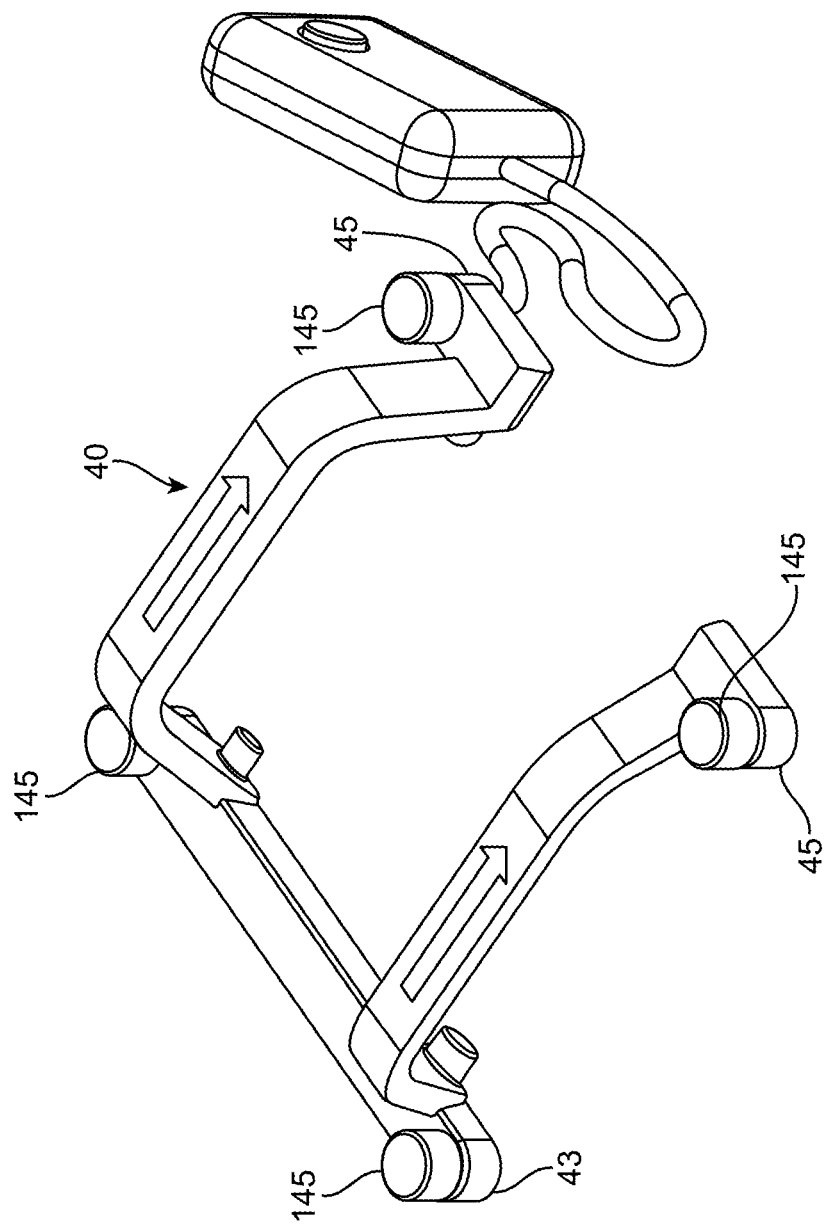
FIGS. 27A and 27B depict another embodiment of a sensor array having additional (8) paired sensors alone and mated with a foundation plate and registration device, respectively.
Figure 27B:
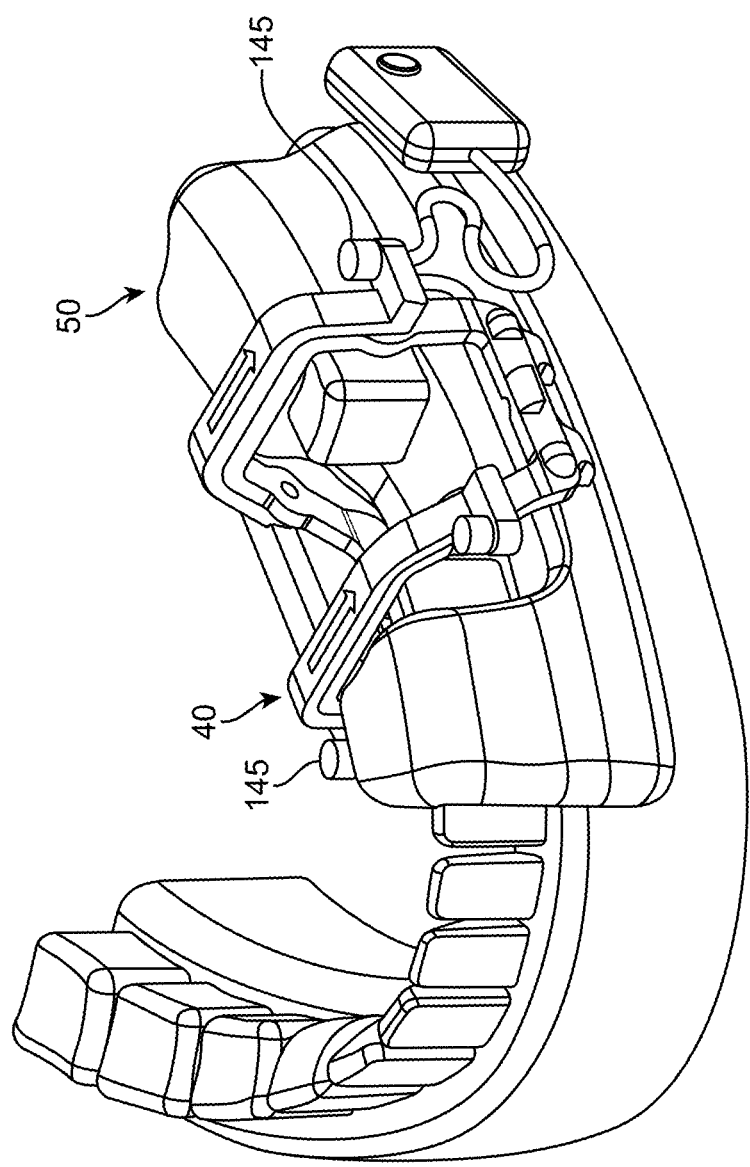

In a frequent embodiment, as depicted in FIG. 14, four electromagnetic sensors in a perfect square are embedded in the lower portions 43, 45 of the sensor array 40. In another frequent embodiment, as depicted in FIGS. 27A and 27B, eight electromagnetic sensors are provided embedded in the lower portions 43, 45 of the sensor array 40 with a paired sensor situated above the sensor embedded in the sensor array. Whether the sensor is embedded in the material of the sensor array is often inconsequential to the operation of the sensor array. Though electromagnetic sensors are exemplified, other conventional mechanisms of sensing the placement, angulation, and/or orientation of a surgical tool such as a drill bit are contemplated in certain limited embodiments. For example, U.S. Pat. Nos. 6,665,948, 7,457,443, 8,224,025, and 8,734,153, and U.S. Patent Application Pub. Nos. 20050116673 and 20120237892, each of which is incorporated herein by reference.

In use, the location and angular orientation of the drill bit of the dental handpiece relative to the sensors is determined and related data is sent to a computer system for display alone, or more frequently overlaid on a CT image of the anatomy of a subject. Frequently, an image of the patient's dentition and a depiction of the location and angular orientation of the drill bit is displayed. See, e.g., FIG. 13, 15. The image can be provided in a variety of levels of granularity, including a depiction of the drill bit itself, or representations of the drill bit in the form of vectors, lines, colorings, or other indicators. Cues in the form of physical feedback such as a vibration are also contemplated. In certain embodiments, the positioning and orientation of the drill bit may be indicated through generic indicators such as a typed or spoken word, a noise, or a color. These indicators are based on the location, tilt, offset, and depth of the drill bit are calculated by the system using an algorithm relative to the representation of the anatomy of the subject generated using the radiographic scan and may optionally be provided to the dentist using above-noted or other similar non-visual cues, or in replacement of visual representation thereof. Often, visual representations are provided on a display, optionally with real time data or images overlaid on a static or real-time image of the anatomy of a subject. Multiples of any one of these or combinations of any two of more of these types of indicators are contemplated embodiments. In one embodiment, the system provides only an auditory accounting of the tilt, offset, and/or depth during the procedure. In one embodiment, the system provides only a physical feedback (e.g., vibratory) accounting of the tilt, offset, and/or depth during the procedure. In another embodiment, the system provides both a visual and an auditory accounting of the tilt, offset, and/or depth during the procedure. In other embodiments, the system provides only a visual accounting of the tilt, offset, and/or depth during the procedure. In another embodiment, the system provides both an auditory and physical feedback accounting of the tilt, offset, and/or depth during the procedure. In another embodiment, the system provides both a visual and physical feedback accounting of the tilt, offset, and/or depth during the procedure. In another embodiment, the system provides a visual, auditory, and physical feedback accounting of the tilt, offset, and/or depth during the procedure. The present disclosure includes receiving real-time data from the sensor system, and determining from the updated data an updated location and angular orientation of the drill bit in relation to the anatomy of the subject. The image on the display and/or auditory signal is updated and adjusted to provide the updated location, tilt, and offset orientation of the drill bit in relation to the anatomy of the subject. In this way, real time feedback is shown, indicating how the drill bit correlates to the anatomy of the subject.

Figure 17:
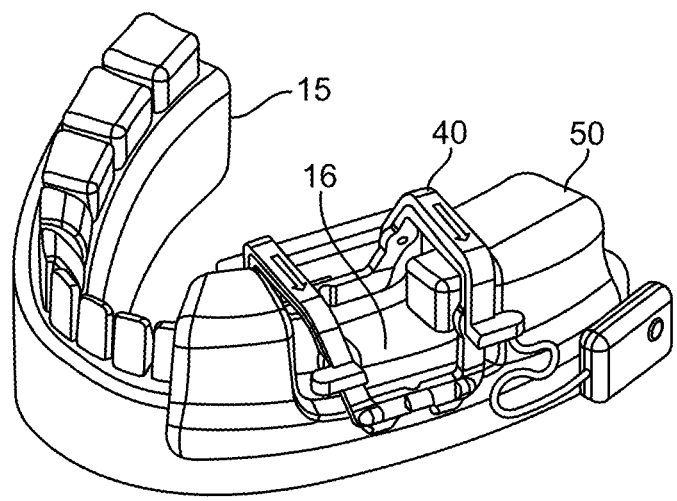
FIG. 17 depicts an exemplary sensor array of the present disclosure mated with the foundation plate of an exemplary registration device positioned on a representation of the anatomy of a subject.

The placement of the electromagnetic sensors in the lower portions 43, 45 of the sensor array 40 is a significant development and innovation. Placement in the lower portions 43, 45 places the sensors close to or at the surface of the bone of the jaw of the subject at or near the implant site 16. As can be seen in FIG. 17, for example, the lower portions 43, 45 are below the top of the teeth 17 and at, near, or approaching the bone of the jaw 15. In other words, the electromagnetic sensors of the sensor array 40 are oriented vertically at or approaching the top of the bone of the jaw 15, thus providing sensor coverage very close to the entry point of a drill into soft tissue and bone of the jaw 15. The inventors have determined that placement of the sensors close to the bone of the jaw 15 of a subject is beneficial versus the prior proposed methods and apparatus. For example, the distance that the drill bit must travel prior to contacting the anatomy of the subject after passing through the sensors is minimized for better accuracy of depth, tilt, and offset, determinations for the bore hole. Moreover, the distance that the drill bit has to travel after exiting a drill bit sleeve (if used) is minimized, thus providing better stability to the drill bit and enhanced safety for the subject.

Exemplary sensors are located near the gum line, instead of being clustered close together around the drill hole at a high level well above the tooth surfaces. In frequent sensor arrays 40, exemplary electromagnetic sensors are also spatially spread out beyond the boundaries of teeth 17 and gums of the subject, but at or adjacent to the gum line 15 and away from the implant site 16. The implant site 16 is therefore more accessible and unencumbered, with excellent access and visibility and far greater accuracy. These sensors pick up the movement of a drill bit very close to the implant site to ensure proper directional accuracy and depth monitoring and calculations. The sensors can provide a real-time representation of the position of the drill bit relative to the implant site. Often, a drill position indicator is overlaid and co-displayed with one or more images from the radiographic scan.

The sensor array exemplified herein is not intended to be limited to any particular materials or physical arrangement with the limitation that it provides reliable placement of a sensor at about the anatomy or implant site of a subject (such as a gumline) intended for radiographic investigation or surgical intervention.

Importantly, a conventional dental drill handpiece can be utilized in conjunction with the present devices, systems, and kits. This drill handpiece need not be modified and add-on devices or sensors for the handpiece are unnecessary according to the present disclosure.

As also indicated, the sensor array 40 also includes a data transponder 41 such as a blue tooth transponder 41. Though a Bluetooth transponder is preferred, any known mode of data transfer could work in the present systems and methods that have the capability of transmitting data about the spatial orientation or other information about a surgical instrument detected by the sensors of the sensor array 40. Other exemplary data transfer modes include touch memory, radio-frequency identification (RFID), wired connection, or other modes. The data transponder 41 is generally dimensioned physically such that it will fit between the gum and cheek of a subject throughout an implant procedure. In frequent embodiments, the transponder is provided with a portable and limited time duration power source, such as a battery. Often the battery power is capable of providing power to the transponder for a limited time. This "limited time" is often about 30 minutes or less. Most frequently, the limited time is less than two hours, less than an hour, or less than 45 minutes. As many of the devices of the present disclosure are intended to be disposable to ensure that they cannot be re-used on multiple patients to reduce cross-contamination and to enhance accuracy, a power source having a limited time duration is a frequent option. For example, once the transponder 41 is activated, the power source is capable of transmitting data for a limited time as noted above. The transponder provides registration of the sensor array with the computer system to provide real-time indication or visualization of the drill bit. The transponder may be permanently attached or releasably connected with the sensor array. In certain embodiments, the transponder is releasably attachable to one or more sensor array.

In some embodiments, a software application of the sensor system combines the location and orientation data for the drill bit, fiducial references, designed implant location, depth, tilt, and offset, and provides real-time information to the dentist of the drill bit progress relative to the anatomy of the subject. Often, the software algorithm calculates the location and/or orientation of the drill bit relative to the desired implant shaft, the planned depth of the implant bore or other anatomical structures near or adjacent to the bore. Also often, the system provides a warning message or indication to the dentist if the drill bit tilt, offset, or depth deviates beyond a pre-set threshold from the desired parameters. The warning message or indication, as noted herein, is provided in a visual, auditory, and/or physical feedback manner. Prior to drilling into available bone, the dentist may optionally move gingival tissue via conventional methods by, for example, incising to form a flap.

In frequent embodiments, the registration device 50 is used together with the sensor array 40 during an implantation procedure. Often, the registration device 50 is used together with the sensor array 40 during an implantation procedure without the use of a physical drill guide 96.

Physical Drill Guide

The present disclosure also contemplates the use of a drill guide that provides physical orientation of a drill bit in a surgical procedure. The description below outlines some characteristic features of the methods and apparatus utilized in these embodiments.

With reference to FIGS. 18-23, an angle setter 60 apparatus is described that facilitates the fabrication of a physical guide that can be used together with the foundation plate 20 or registration device 50. In the most frequent embodiments, the angle setting apparatus is not disposable, as that term is used herein. The purpose of the fabrication is to create a device (together 80 & 90) that ensures the tilt and offset angles determined in a radiographic scan (e.g., CT scan), as explained above, as the optimal drill angles for an implant procedure for a specific subject can be replicated during a surgical procedure on that subject.

Figure 18:
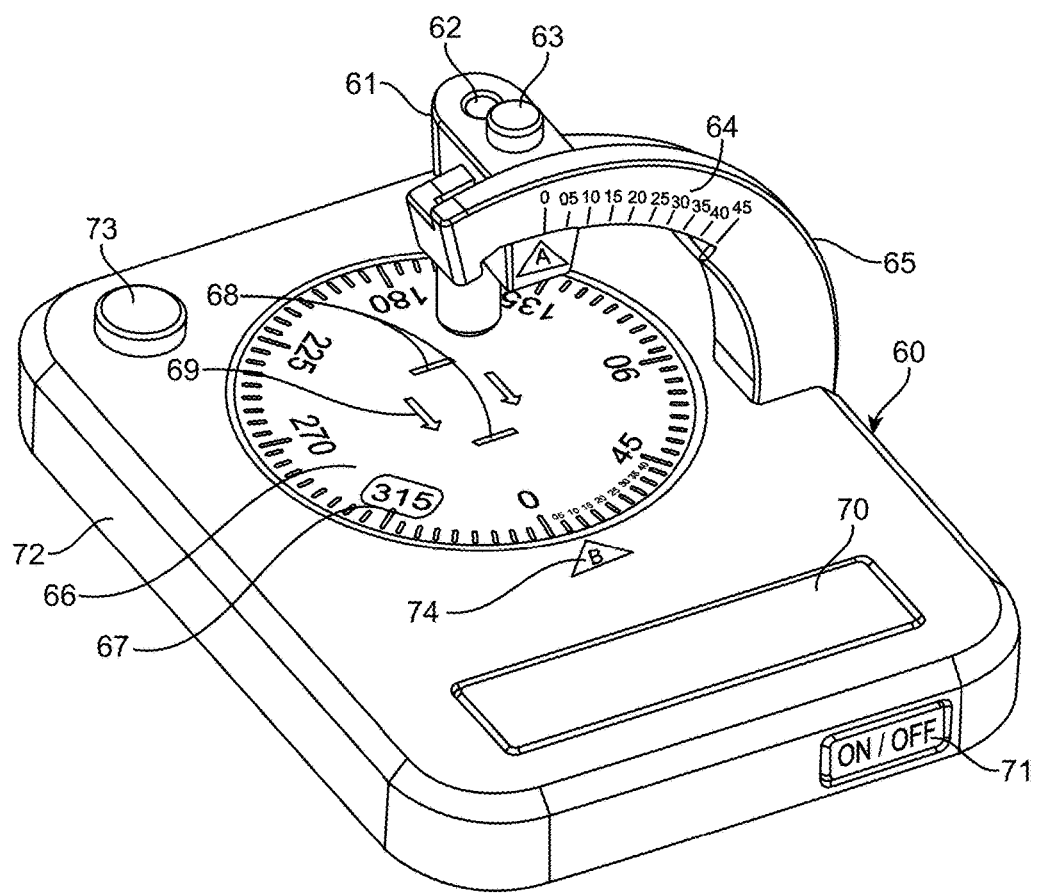
FIG. 18 depicts a perspective view of an exemplary angle setter of the present disclosure.

FIG. 18 depicts an exemplary angle setter 60 of the present disclosure. This angle includes some or all of the following features. A hole 62 is for a collar pin 91 and an actuating mechanism such as a knob 63 for locking the angle arm head 61 in place in a predetermined orientation on the angle arm 65. The angle arm head 61 can often move in an arc across the angle arm 65, most frequently up to 90 degrees of angular travel, but most frequently within 45 degrees of vertical, or within 30 degrees of vertical. The angle arm often includes analog/physical angular settings 64 to show the placement of the angle arm head 61 on the angle arm 65. A swivel base 66 is included that can rotate in one or two directions up to about 360 degrees of rotation, or is capable of rotating freely in the angle setter base 72. An actuating mechanism such as a knob 73 is included to lock the swivel base in place in a predetermined orientation. The swivel base 66 often includes analog/physical angular settings 67 to show the placement of the swivel base 66 within the base 72 and with respect to the location of the angle arm 65 or a centering mark 74. The swivel base 66 includes a feature 68 to support a guide base 80 and directional indicia 69 to ensure proper placement of the guide base 80 on the swivel base 66 to provide accurate angular placement of the guide collar 90. An optional digital display 70 is electronically coupled to the angle arm head 61 and the swivel base 66 and shows the angular readout of the angle arm head (angle A) and swivel base (angle B). The angle arm head 61 rotates for proper angular adjustment of angle A. The swivel base 66 rotates for proper angular adjustment of angle B. The power button 71 turns the digital readout 70 on and off. Rotation of the swivel base 66 and travel of the angle arm head 61 can be manual or automated.

Figure 19:
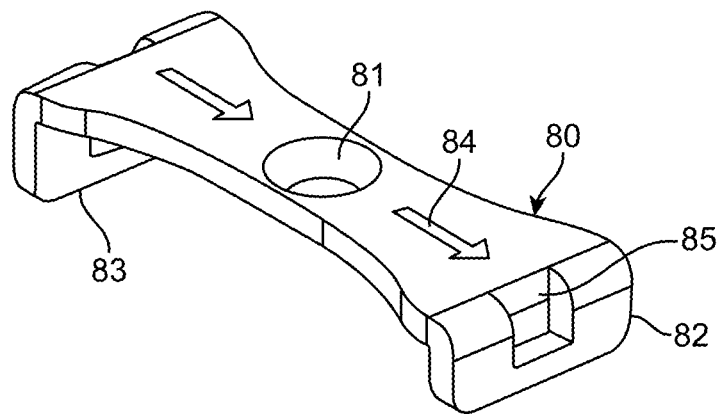
FIG. 19 depicts an exemplary guide base of the present disclosure.
Figure 20:
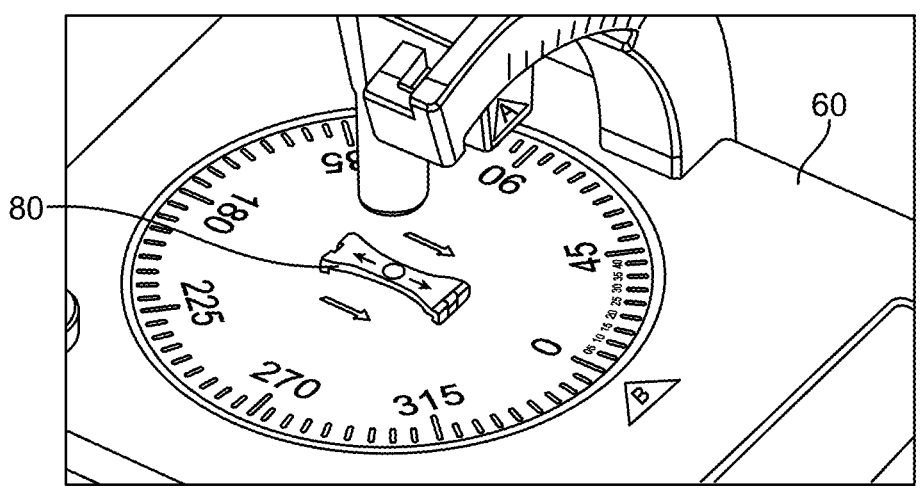
FIG. 20 depicts an exemplary guide base positioned on an angle setter.

When using an exemplary angle setter 60 having a digital display, the dentist begins by initiating the digital readout 70 of the angle setter 60. The calibration of the angle setter 60 is verified, for example, by comparing the analog/physical settings 64, 67 on the swivel base 66 and angle arm 65 with those displayed on the digital readout 70, 75. With reference to FIGS. 19-20. The dentist removes a fresh guide base 80 from its packaging and places it into the angle setter 60. The guide base 80 often includes directional indicia 84 and the guide base 80 is placed in feature 68 on the swivel base 66 in an orientation that aligns with the directional indicia 69 of the swivel base 66. The guide base 80 also frequently includes a physical feature or features such as lips 82, 83, each having different dimensions, to ensure proper placement of the guide base on swivel base 66 and foundation plate 20. Most frequently, the guide base 80 includes a base opening 81 having surrounding chamfered edges for positioning of a guide collar 90. Features 85, 86 also can be provided to physically cooperate with features 25 of the foundation plate 20 to attachment thereto.

Figure 22:
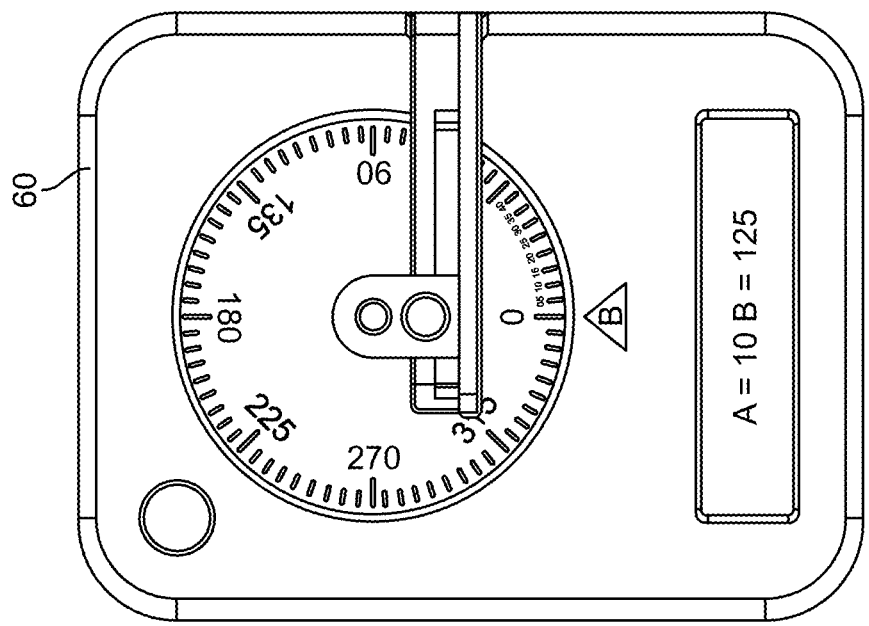
FIG. 22 depicts an angle setter installing a guide collar on a guide base to create a drill guide.
Figure 21:
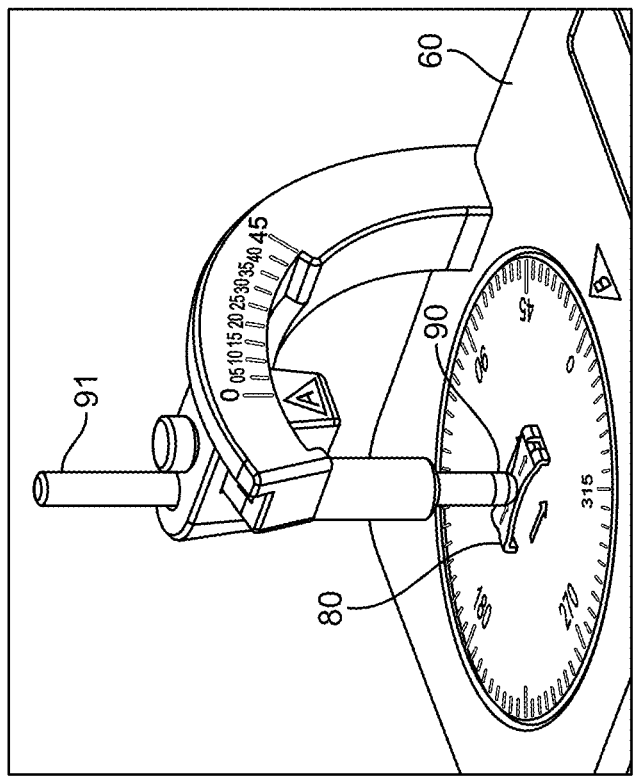
FIG. 21 depicts a top view of an angle setter displaying exemplary tilt and offset angles.
Figure 23A:
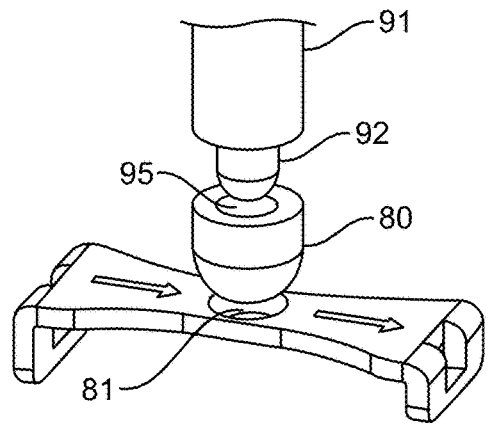
FIGS. 23A, 23B, and 23C depict a collar pin installing a guide collar on a drill guide base to create a drill guide.
Figure 23B:
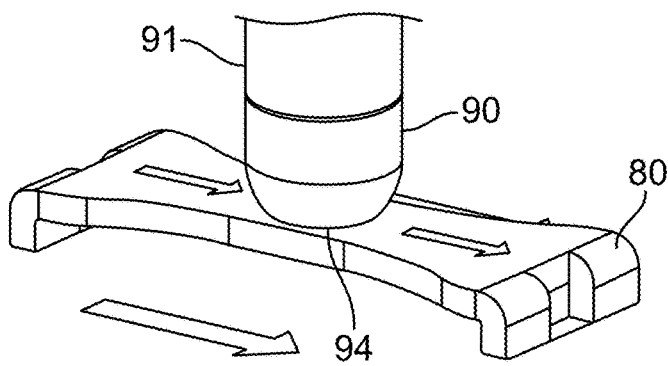
Figure 23C:
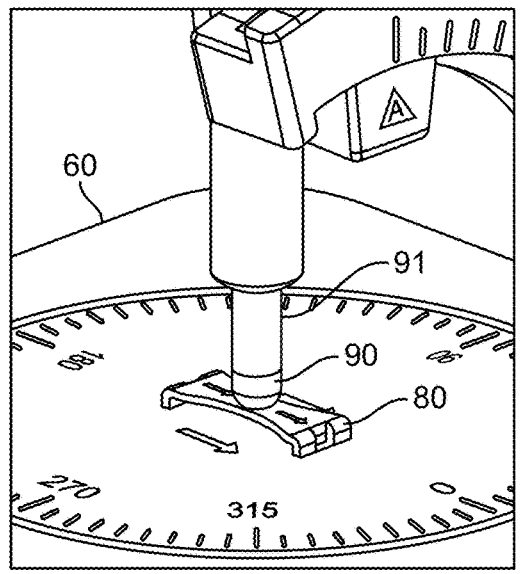

With reference to FIGS. 21-23, the dentist then adjusts the angle setter 60 to the angles generated by the implant software, for example, starting with angle "A" and locking it in place with actuating mechanism 63. Optionally, the software is connected with the angle setter 60 such that the adjustments necessary for the angle adjuster are set automatically by the software or an interface between the software and the angle setter 60. Angle "B" is also adjusted and locked it into place with actuating mechanism 73. With angles A and B set, the angulation for the collar pin 91 to adjust the guide collar 90 is set. The dentist then chooses a specified size guide collar 90, which acts in frequent embodiments as a drill depth control. The guide collar 90 size can optionally be provided or suggested by the implant software based on the physical features of the anatomy of the subject as they were determined from the radiographic scan. A variety of sizes are contemplated, including heights such as 0.5 mm, 1 mm, 2 mm, 3 mm, 4 mm, 5 mm, 6 mm, 7 mm, 8 mm, 9 mm, 10 mm or larger, including intervals therebetween. The guide collar 90 contains a central opening 95 that is designed to accommodate one or more drill bit sizes or one or more drill bit sleeve sizes. This central opening 95 is most frequently operable to be at least partially coaxially situated or co-extensive with the base opening 81. For example, when the guide collar 90 is affixed to the guide base 80, an opening extends through the central opening 95 from the top of the guide collar 90 to the bottom of the guide collar 90 and out through the base opening 81.

A collar pin 91 is then passed through hole 62 (FIG. 18) and a tip 92 of the collar pin 91 is inserted into the central opening 95 of the top of a guide collar 90 to align the guide collar with the angulation of the collar pin 91 as it sits in an indentation 84 of the guide base 80. The collar pin 91 applies a force 93 to capture the guide collar 90 against the guide base 80. The dentist then applies an adhesive to the drill guide collar 90 and/or guide base 80 (area noted as aspect 94), to adhere them together and setting the tilt and offset of the guide collar 90. The adhesive may be of the type that is cured using UV light, such as a light-activated resin. Similar dental adhesives and cements, light cured and non-light cured, are known in the art and are also contemplated in the embodiments described herein. Though adhesive is exemplified, other methods of permanent or semi-permanent attachment of the guide collar 90 to the guide base 80 are contemplated, including snap-fit attachments and co-molding. In certain limited embodiments, the guide base 80 and guide collar 90, individually or together including the requisite tilt and offset angulations, are fabricated by a 3-D printer.

Figures 24A, 24B:
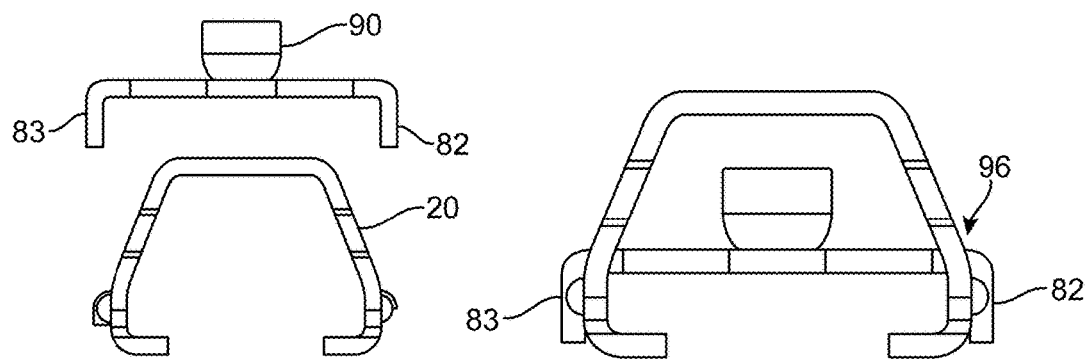
FIGS. 24A, 24B, and 24C depict a drill guide both before and after mating with a foundation plate and a registration device.
Figure 24C:
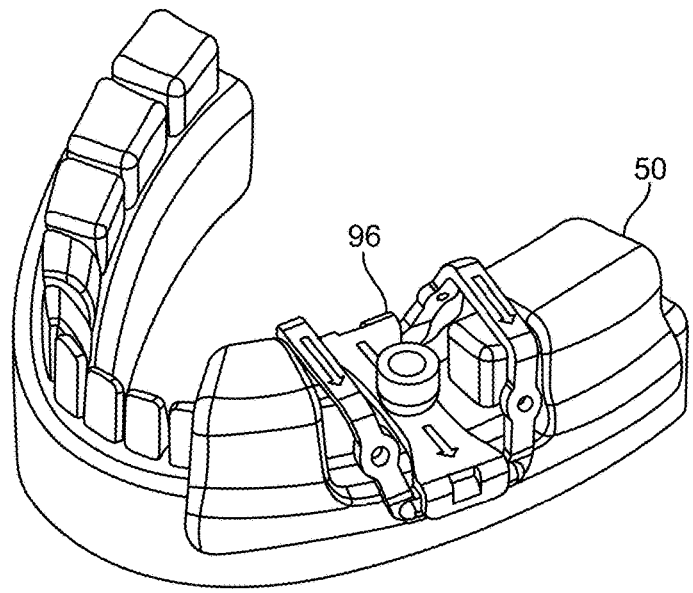
Figure 25:
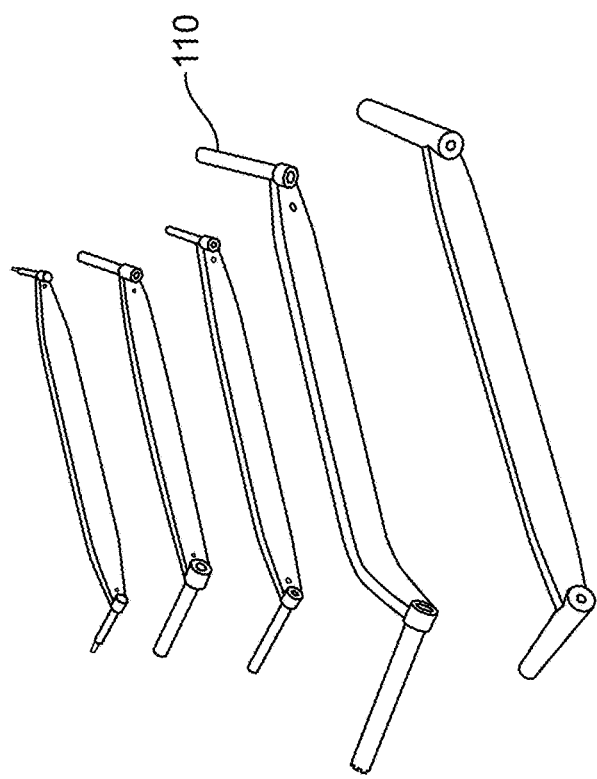
FIG. 25 depicts various drill bit sleeves accepted by the drill guide.

Once the physical drill guide 96 (also referred to herein as a "physical guide") is fully cured, it can be removed from the angle setter 60 and clipped in place on the registration device 50. FIGS. 24A-24C. The device is then placed onto the anatomy of the subject. The dentist can then begin the implant procedure, using interchangeable drill bit sleeves FIG. 25, 110 according to the size of drill bit being used.

In certain embodiments, the physical drill guide is used without the sensor array. In such embodiments, real-time data regarding the orientation and depth are not provided on a computer system. Rather, the physical drill guide 96 is operable according to the methods described herein using apparatuses having the functionalities described herein to provide the requisite orientation and depth stop for the drill bit. The orientation and drill bit depth stop are determined, for example, using radiographic scan information using the registration device 50. The choice of size of the guide collar 90 provides the drill-bit depth stop and the orientation of the guide collar 90 on the guide base 80 is operable, for example, to match information obtained from the radiographic scan and implant software, if utilized.

The physical guide exemplified herein is not intended to be limited to any particular materials or physical arrangement with the limitation that it provides reliable placement of a physical guide for a drill-bit that is custom set to the specific orientation and depth required to carry out a surgical intervention and is placed at about the anatomy or implant site of a subject (such as a gumline) intended for radiographic investigation or surgical intervention.

Hybrid Physical and Sensor Guides

Figure 26:
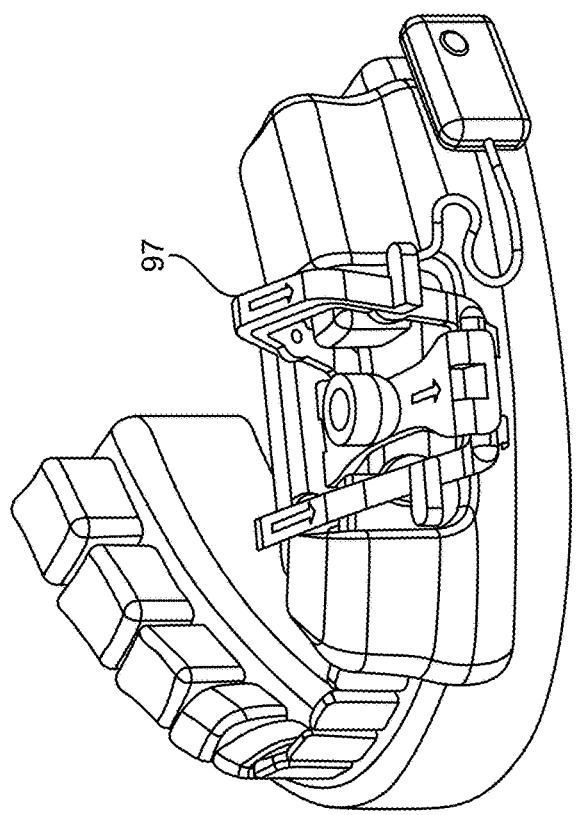
FIG. 26 depicts a drill guide and a sensor array mated with a registration device positioned on the anatomy of a subject.

In addition to the sensor and physical guide embodiments of the drill guide described herein, another collection of embodiments is contemplated and described that involves the combination of some or each of the features of the sensor and physical guide embodiments into a hybrid physical and sensor drill guide 97. An exemplary embodiment is depicted in FIG. 26—each of the features of these embodiments is described elsewhere herein. In its use, upon confirmation of the working sensor array, the dentist then clips the sensor array 40 onto the foundation plate 20 of the registration device 50. The physical drill guide 96 is often attached to the foundation plate 20 of the registration device 50 prior to attachment of the sensor array 40. Similar to the physical drill guide and sensor only drill guides above, together the registration device 50, physical drill guide 80, 90 and the sensor array 40 form a unit when attached that is intended to be disposed after use in designing and carrying out an implant procedure.

In use the hybrid device is placed onto the anatomy of the subject and the dentist can then begin an implant procedure using interchangeable drill bit sleeves 110 with the Physical Guide, according to the size of drill bit being used. Sensor feedback will also be shown on the system screen on the implant software. This arrangement pre-determines and sets a proper drill path without a dentist having to guess where to go or struggle with visibility and a cumbersome high level drill guide. Significantly, using the hybrid or sensor guides described herein provides visual confirmation of the correct drill pathway in real time on the computer monitor. Unlike trying to achieve this benefit by using a currently available computer generated drill guide with a pre-set hole requiring a pathway that starts well above the tooth surface level and requires extra-long drill bits, the present systems provide the dentist, not the lab, full control over the entire pre-set or fabrication process. The dentist can now see everything clearly through the use of the hybrid guide, which combines an accurate mechanical pre-set pathway and visual confirmation that the drill bit is entering and passing through bone exactly where it belongs. Moreover, in each of the embodiments described herein the dentist has an open and accessible work area defining the implant site that can be viewed directly during an implant procedure while the physical guide, sensor, or hybrid drill guide embodiments are being utilized with a subject.

Other features and advantages of the invention will be apparent from the following detailed description, and from the claims.

The present invention is described or illustrated using a variety of examples provided herein. The examples are provided solely to illustrate the invention by reference to specific embodiments. These exemplifications, while illustrating certain specific aspects of the invention, do not portray the limitations or circumscribe the scope of the disclosed invention.

Moreover, while dental implantation provides the majority of the embodiments described herein, the disclosure is not intended to be limited to such embodiments. Rather, without departing from the overall thrust of the present disclosure, the teachings may be readily applied to surgical interventions or radiographic analyses involving additional portions of a subject's anatomy.

Citation of the above publications or documents is not intended as an admission that any of the foregoing is pertinent prior art, nor does it constitute any admission as to the contents or date of these publications or documents.

We claim:

1. A surgical guide device comprising
   one or more electromagnetic sensors, wherein the surgical guide device is operable to position the one or more sensors at about the gumline of a subject when the surgical guide is removably positioned at an implant site on the subject;
   a sensor array having an open arched material defined by a first and second upper portion perpendicularly situated to a lower portion, each upper portion having a pair of bilateral sloping arms, wherein the lower portion is connected to at least one of the pair of bilateral sloping arms of each of upper portions;

at least one of the one or more electromagnetic sensors included in the lower portion; and a transponder in communication with the sensor and configured to transmit data received by the sensor to a remote processor.

2. The surgical guide device of claim 1, wherein the transponder is powered with a low power battery.

3. A radiographic guide device comprising one or more fiducials, wherein the radiographic guide device is operable to position the fiducials at about the gumline of a subject when the radiographic guide is removably positioned at an implant site on the subject;

wherein the radiographic guide comprises an open arched material defined by a first and second upper portion perpendicularly situated to a first and second lower portion, and two or more fiducial markers, each upper portion having a pair of bilateral sloping arms connecting the first and second upper portions to the first and second lower portions, wherein each of the lower portions comprises a laterally extending foot prong.

4. The radiographic guide device of claim 3, wherein at least one of the pair of bilateral sloping arms comprises an attachment point for a secondary device.

5. The radiographic guide device of claim 3, wherein at least one of the lower portions comprises an attachment point for a secondary device.

6. The radiographic guide device of claim 3, wherein the open arched material defines an open surgical area that is unimpeded both (a) vertically; and (b) laterally, parallel to the first and second upper portions and above the lower portions.

* * * * *